US006438398B1

(12) United States Patent
Pflugfelder et al.

(10) Patent No.: US 6,438,398 B1
(45) Date of Patent: Aug. 20, 2002

(54) PROCESS AND DEVICE FOR MEASURING TEAR FLUORESCEIN CLEARANCE

(75) Inventors: Stephen C. Pflugfelder; Scheffer C. G. Tseng; Adolfo Afonso, all of Miami, FL (US); Angelo Macri, Genova (IT)

(73) Assignee: The University of Miami, Miami, FL (US)

( * ) Notice: Subject to any disclaimer, the term of this patent is extended or adjusted under 35 U.S.C. 154(b) by 0 days.

(21) Appl. No.: 09/518,693

(22) Filed: Mar. 3, 2000

Related U.S. Application Data
(60) Provisional application No. 60/123,172, filed on Mar. 5, 1999.

(51) Int. Cl.[7] ................................................. A61B 5/00
(52) U.S. Cl. ...................................................... 600/321
(58) Field of Search ................................ 600/321, 356; 385/901; 356/317

(56) References Cited

U.S. PATENT DOCUMENTS

| | | | |
|---|---|---|---|
| 4,043,675 A | * 8/1977 | Guennel et al. | ............. 385/901 |
| 5,540,227 A | 7/1996 | Poole | |
| 5,616,502 A | * 4/1997 | Haugland et al. | ............. 436/86 |

FOREIGN PATENT DOCUMENTS

| EP | 0 426 307 A2 | 5/1991 |
|---|---|---|

OTHER PUBLICATIONS

Prabhasawat et al., "Frequent Association of Delayed Tear Clearance in Ocular Irritation", British Journal of Ophthalmology, vol. 82, (Jun. 1998), pp. 666–675.

Xu et al., "Correlation of Tear Clearance Rate and Fluorophotometric Assessment of Tear Turnover", British Journal of Ophthalmology, vol. 79 (1995), pp. 1042–1045.

Afonso et al., "Correlation of Tear Fluorescein Clearance and Schirmer Test Scores With Ocular Irritation Symptoms", Ophthalmology, vol. 106, (Apr. 1999), pp. 803–810.

Jones et al., "A Novel Method of Tear Collection: Comparison of Glass Capillary Micropipettes With Porous Polyester Rods", Cornea, vol. 16, No. 4, (1997), pp. 450–458.

Macri et al., "A Standardized Visual Scale for Evaluation of Tear Fluorescein Clearance", Ophthalmology, vol. 107 (Jul. 2000), pp. 1338–1343.

Zappia, Robert J. M.D. et al, Lacrimal Drainage Function, American Journal of Ophthalmology, vol. 74 No. 1, p. 160–162, Jul. 1972.*

* cited by examiner

Primary Examiner—Eric F. Winakur
Assistant Examiner—David McCrosky
(74) Attorney, Agent, or Firm—Pillsbury Winthrop LLP

(57) ABSTRACT

A method of evaluating clearance of fluorescein dye instilled into tear film having a greater sensitivity and specificity for diagnosing a tear film disorder as the cause of a patient's ocular irritation and ocular surface disease than can be achieved using the traditional methods. The inventive method can be performed using a diagnostic kit for evaluating tear fluorescence clearance in which the concentration of tear fluorescein is visually quantified via a color standard.

32 Claims, 21 Drawing Sheets

PROCESS AND DEVICE FOR MEASURING TEAR FLUORESCEIN CLEARANCE

This application claims the benefit of U.S. Provisional Application No. 60/123,172, filed Mar. 5, 1999.

This invention was developed using funds received from the United States Department of Health and Human Services, National Eye Institute under grant EY 11915. The United States government may have certain rights to this invention.

BACKGROUND OF THE INVENTION

1. Field of the Invention

The invention relates to a diagnostic kit for measuring tear clearance and a method of measuring tear clearance from a mammalian eye.

2. Description of Related Art

Ocular irritation is one of the most common complaints of patients presenting to the eye care practitioners. The exact mechanism by which eye irritation symptoms develop has been not established. Most patients presenting with ocular irritation have a reduced tear break-up time indicating the presence of tear film instability. This may be due to decreased aqueous tear production, meibomian gland disease that leads to lipid tear deficiency or undefined causes. Pathological changes of the meibomian glands are known to be present in many asymptomatic, elderly patients. Accordingly, the exact pathogenic role of these changes remains unclear.

The National Eye Institute/Industry Workshop on dry eye proposed a classification scheme that stratified dry eye patients into those with aqueous tear deficiency due to lacrimal gland disease or dysfunction and those with evaporative tear loss. Development of this classification scheme represented an important step in standardizing the diagnosis and classification of dry eye. While some patients present with clearly defined dry eye conditions such as Sjögren's syndrome aqueous tear deficiency or meibomian gland disease following Accutane™ therapy, many patients present with a combination of clinical problems contributing to their tear film deficiency (e.g. aqueous tear deficiency, meibomian gland disease, incomplete blink, lid laxity and conjunctivochalasis).

Pflugfelder et al. previously observed that delayed clearance of fluorescein dye instilled into the tear film is frequently found in patients complaining of ocular irritation, even in those with normal aqueous tear production (See Pflugfelder S C, Tseng S C G, Sanabria O, et al. *Cornea.* 1998; 17:38–56). Furthermore, as tear clearance decreases, the concentration of pathological factors in the tear film capable of inciting inflammation, for example, Il-1α, and tissue destruction, for example, matrix metalloproteinase (MMP-9), increases. These findings suggest that delayed tear clearance leads to chronic ocular surface inflammation, which in turn could sensitize the nerves that are responsible for the irritation symptoms.

A number of different techniques are known in the art for measuring the clearance or turnover of fluorescein instilled into the tears, including direct fluorometric measurement of fluorescein in the pre-corneal tear film or the inferior tear meniscus (See Benedetto D A, Clinch T E, Laibson P R. *Arch Ophthalmol* 1984; 102,410–2). A more practical method is to visually compare the fluorescein concentration in tear fluid collected on Schirmer test strips to photographic standards (See Nava A, Barton K, Monroy D C, Pflugfelder S C. *Cornea* 1997; 16:430–438). This Schirmer strip method has been reported to have excellent correlation with in vivo fluorometric measurement of basal tear turnover and tear flow. Nevertheless, this semiquantitative technique is not optimal for correlating tear clearance with the concentration of pathogenic factors in the tear fluid (e.g. IL-1) or for monitoring small changes in tear clearance that may occur in therapeutic clinical trials. Previous studies evaluating patients complaining of ocular irritation reported poor correlation between the severity of irritation symptoms and the Schirmer test (either the Schirmer 1 or the basic secretion test) and only moderate correlation with corneal or ocular surface dye staining (See Afonso A A, Monroy D, Stern M E, Feuer W J, Tseng S C, Pflugfelder S C. *Ophthalmology* 1999;4:803–810). This may be due in part to the fact that symptomatic patients with meibomian gland disease often have normal or only minimally reduced aqueous tear production. This suggests that factors other than aqueous tear deficiency play a role in the pathogenesis of dry eye. Afonso and colleagues have observed better tear fluorescein clearance correlation with ocular irritation symptoms than with the Schirmer 1 test (See Afonso et al., supra). Jones and associates reported a technique of obtaining tear fluid from the inferior meniscus with a polyester rod. These low protein-binding rods have been used to obtain well-mixed tear fluid from the inferior tear meniscus for measuring tear cytokine concentrations (See Nava et al., supra). In dry eye patients, the pre-comeal tear layer may break-up rapidly and overlies a diseased corneal epithelium that is excessively permeable to fluorescein, making it difficult to determine whether fluorescein readings are from tear fluid or corneal tissue.

Regardless of the underlying cause, patients with tear film deficiencies complain of irritation symptoms and often show ocular surface epithelial, eyelid marginal and meibomian gland diseases. Even though the cause of these problems has not been established, better means of detecting such ocular abnormalities affecting tear flow are needed.

SUMMARY OF THE INVENTION

The inventive technique eliminates well-known problems associated with assessing fluorescein concentration in the precorneal tear film in vivo.

An embodiment of the invention provides a method of measuring tear clearance from a mammalian eye, comprising:

(a) instilling an effective amount fluorescein dye solution into the inferior conjunctival sac of an eye;
(b) incubating the fluorescein dye solution in the conjunctival sac for a period of time sufficient to allow the dye to mix with tear fluid;
(c) collecting a sample of tear fluid from the eye;
(d) determining the volume of tear fluid collected; and
(e) measuring the amount of fluorescence present in the tear fluid.

Another embodiment of the invention provides for a process of detecting at least one ocular abnormality affecting tear flow, said process comprising:

(a) instilling an effective amount fluorescein dye solution into the inferior conjunctival sac of an eye;
(b) incubating the fluorescein dye solution in the conjunctival sac for a period of time sufficient to allow the dye to mix with tear fluid;
(c) collecting a sample of tear fluid from the eye;
(d) determining the volume of tear fluid collected; and
(e) measuring the amount of fluorescence present in the tear fluid, wherein preferably said at least one ocular abnormality comprises a member selected from the group consisting of meibomian gland disease, conjunctivochalasis, lid laxity, tear outflow obstruction and blink abnormalities.

Another preferred embodiment is a process of detecting at least one ocular abnormality affecting tear flow, said process comprising:

(a) instilling an effective amount of fluorescein dye solution into the conjunctival sac of an eye;

(b) incubating the fluorescein dye solution in the conjunctival sac for a period of time sufficient to allow the dye to mix with tear fluid;

(c) examining the eye surface with a biomicroscope to observe corneal fluorescein staining in each of four corneal quadrants;

(e) measuring the amount of fluorescence observed to obtain a corneal fluorescein staining score; and (f) correlating the corneal fluorescein staining score with results from a Fluorescein Clearance Test (FCT) corrected according to correction formula I:

$$FCT(\text{corrected}) = FCT + \text{Schirmer score } y \qquad \text{I}$$

wherein coefficient y is calculated from a corresponding area under the Receiver Operating Characteristic (ROC) curve, and the Schirmer score is obtained using Schirmer test strips placed over an eyelid margin.

Still another embodiment of the invention provides for a diagnostic kit for measuring tear clearance. The kit may comprise an indicator that may be directly measured in the inferior tear meniscus of the eye. The kit may contain, for example, a fluorescein dye as an indicator.

Yet another embodiment of the invention provides for a diagnostic kit for measuring tear clearance comprising:

(a) a fluorescein dye solution suitable for introduction into the inferior conjunctival sac of an eye;

(b) optionally, a substrate for collecting a sample of tear fluid from the eye; and (c) a color standard for measuring the amount of fluorescence present in the tear fluid.

Another embodiment of the invention provides for a diagnostic kit comprising a color photographic plate as the color standard.

In another embodiment, the kit comprises a fluorescein dye solution to be instilled in the conjunctival sac of an eye, wherein the fluorescein dye solution is administered via a unit-dose dropperette, preferably in dosages of about 0.5 microliters to about 5 microliters of a fluorescein dye solution having a fluoroscein concentration of about 0.1% to about 2.0% fluorescein.

In another embodiment of the invention, a diagnostic kit is provided, in which the color standard comprises a standardized visual scale. Preferably, the sensitivity of measurements from the standardized visual scale are improved according to correction formula II:

$$\text{SVST (corrected)} = \text{SVST} + \frac{\text{Schirmer score}}{y} \qquad \text{II}$$

wherein coefficient y corresponds to an area under a Receiver Operating Characteristic (ROC) curve and the Schirmer score is obtained using Schirmer test strips placed over an eyelid margin.

DETAILED DESCRIPTION OF THE INVENTION

Figure 1:
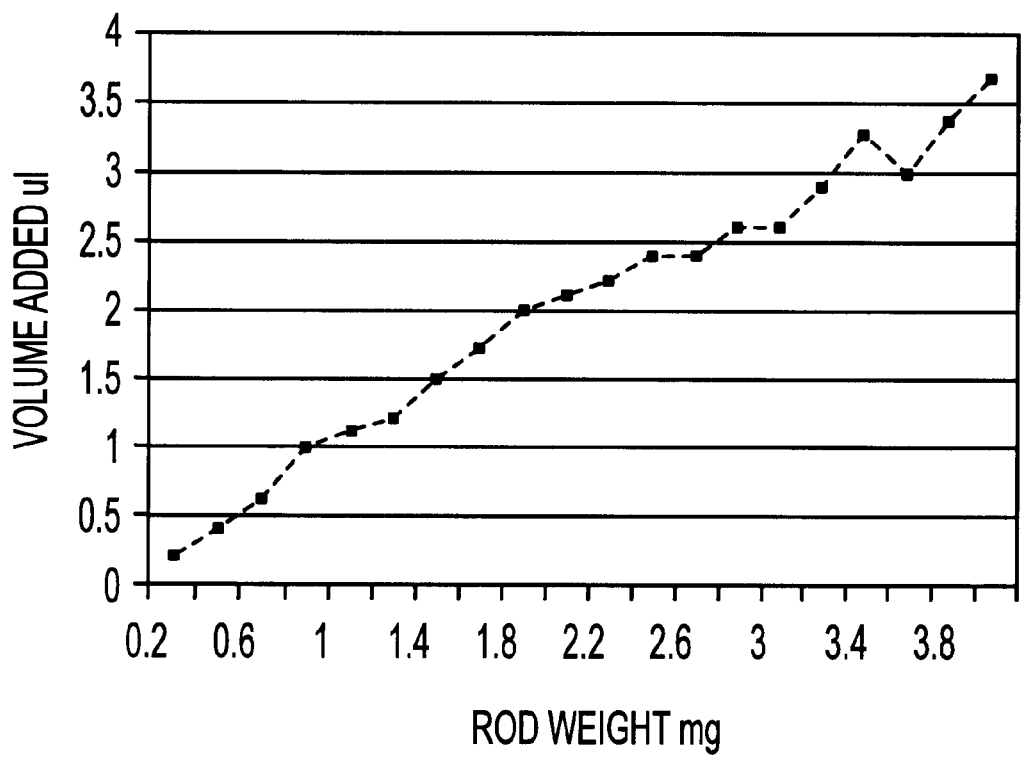
FIG. 1 is a comparison of rod weight vs. volume added to the rod.

In order to accurately measure tear fluorescein concentration, the invention provides a method for measuring the fluorescence of well-mixed tear fluid obtained from the inferior meniscus of the eye with a commercial microtiter plate fluorometer (Cytofluor II). This instrument is commonly used to perform a number of fluorescence assays in many laboratories. The process according to the invention eliminates problems known to be associated with assessing fluorescein concentration in the precorneal tear film in vivo.

In a preferred embodiment of the invention, correlations of the Fluorescein Clearance Test (FCT) and the Schirmer 1 test are made with the severity of corneal epithelial and eyelid disease in normal subjects and patients with tear film disorders due to meibomian gland disease (MGD) and/or aqueous tear deficiency (ATD).

The invention also provides a method for evaluating the correlation and the agreement between a validated fluorometric technique (fluorescein clearance test) and a novel, clinically practical standardized visual scale to evaluate tear fluorescein clearance.

In another preferred embodiment a method is provided for distinguishing normal subjects from patients complaining of ocular irritation associated with meibomian gland disease (MGD) and/or aqueous tear deficiency (ATD).

The invention will be further illustrated in the following non-limiting examples.

EXAMPLES

Example I

An embodiment of the invention comprises correlating and comparing the accuracy of the Schirmer 1 test with an inventive method of measuring tear fluorescein clearance with a CytoFluorII fluorometer for determining the severity of ocular irritation symptoms, clinical signs of meibomian gland disease, corneal fluorescein staining scores and corneal and conjunctival sensitivity.

In order to effectuate these comparisons, a case-control study was designed, comprising 40 abnormal patients presenting with a chief complaint of ocular irritation, and 40 asymptomatic controls of similar age distribution. This study was conducted according to a protocol approved by University of Miami School of Medicine Institutional Review Board and in accordance with the tenets of the Declaration of Helsinki. An informed consent was obtained from each participant after the nature and possible consequences of the study were explained.

As noted hereinabove, two groups of patient subjects were evaluated. The abnormal group included 40 consecutive patients presenting to the Ocular Surface and Tear Center of the Bascom Palmer Eye Institute during a 3 month period between May and July of 1997 with a chief complaint of ocular irritation. These patients had no history of ocular surgery, contact lens use, punctal occlusion or use of eye drops (other than non-preserved artificial tears). Prospective participants were excluded if they had eyelid abnormalities, mechanical problems or conjunctivitis as a cause for their irritation symptoms. The comparison group included 40 normal control subjects of similar age distribution with no history of any eye disease, ocular surgery, use of eye drops, or symptoms of ocular irritation. Subjects were excluded if they used artificial tears on the day of the evaluation. All subjects completed a symptom questionnaire, a baseline ocular examination, fluorescein clearance test (FCT) and Schirmer 1 test. The symptom questionnaire was composed of twelve questions to assess the nature, severity and functional impact of their irritation symptoms. The minimum symptom severity score was zero and the maximum was fifty-six.

A baseline ocular examination was performed to assess i) meibomian gland pathologic changes (orifice metaplasia and percent of acinar drop-out) as previously described (1), ii) corneal fluorescein staining scores using the NEI grading scale (See Lemp, *CLAO J* 1995; 21: 222–32, the disclosure of which is hereby incorporated herein by reference), iii) Schirmer 1 test (without anesthesia) scores, corneal and iv) conjunctival sensitivity with the Cachet-Bonnet anesthesiometer and punctal status (patent or closed).

Severity of ocular irritation was assessed with a symptom questionnaire. Schirmer 1 test, biomicroscopic meibomian gland evaluation, corneal fluorescein staining score and corneal and conjunctival sensation scores with the Cachet-Bonnet anesthesiometer were assessed in all subjects.

Tear fluorescein clearance was assessed prior to performing any other diagnostic tests. This test was performed by instilling about five microliters of a 2% sodium fluorescein solution (IOLAB, Claremont, Calif.) into the inferior conjunctival sac and instructing the patient to carry on normal activities for 15 minutes. However, fluorescein concentrations may range from about 0.5% to about 2% sodium fluorescein. The amount of solution instilled in a patient's eye may vary from between about 0.5 microliters to about 2.0 microliters, depending upon the concentration of fluorescein in the fluorescein solution used. Thereafter, a sample of the tear fluid was collected from the lower tear meniscus as atraumatically as possible to avoid reflex tearing, with a pre-weighed polyester rod (Transorb rods, American Filtrona, Richmond, Va.). The volume of the collected tears was determined by the weight difference between the rod containing the sample and the pre-collection empty rod using an OHAUS Model GA110 scale. Rods were then placed into the end of a micropipette tip located within a 0.5 ml Eppendorf tube as described by Jones and colleagues (See Jones., et al., *Cornea* 1997; 16:450–58, the disclosure of which is hereby incorporated herein by reference), and a volume of phosphate buffered saline (100 µl—weight of rod in micrograms) was added to the end of the rod. The tubes were then spun at 12,000 rpm for 5 minutes and the fluid was transferred to wells of a 96 well polycarbonate microtiter plate (Corning 96, Corning, N.Y.). Fluorescence was measured within 24 hours after collection of the tear fluid using a fluorescence multi-plate reader (CytoFluor II, PerSeptive Biosystems, MA). Samples were protected from the light until fluorescence was measured. The accuracy of the weight measurement was assessed by adding an increasing volume of phosphate buffered saline to the rods then re-weighing them.

The stability of fluorescein in tear samples and the reproducibility of the fluorescence reading were assessed by repeatedly measuring fluorescence over a 24-hour period. The accuracy of the fluorometer was assessed by running reference standards comprising serial dilutions of 2% sodium fluorescein ranging from 0.2% to 0.0002% as controls. If the fluorescein concentration of a sample was greater than the highest control standard, the sample was diluted and fluorescence was re-measured. Tear fluorescein concentration was measured at various sequential time points (5 to 60 minutes) after fluorescein instillation in five normal controls and five Sjögren's syndrome patients to assess the fluorescein clearance kinetics in these eyes.

Statistical evaluation of fluorescein clearance and Schirmer 1 test results was performed on data from the right eye. Specific statistical tests are described hereinbelow.

Assessment of tear fluorescein clearance with the Cytofluor II was accomplished by noting the accuracy of tear volume measurement, the accuracy of the fluorometer, taking repeated measurements of tear fluorescence and determining the kinetics of time required for clearance of fluorescein dye versus tear fluorescein concentration in normal and dry eye patients.

The volume of the collected tears was determined by the weight difference between the rod containing the sample and the pre-collection empty rod. To confirm the accuracy of this measurement, an increasing volume of phosphate buffered saline was added to individual rods and these were re-weighed. FIG. 1 shows that for each 1 μl of saline added, the rod weight increased by 1 mg (95% Confidence interval 1.0, 1.2). The linear correlation between rod weight and added volume was 0.99 (p<0.001).

Figure 2:
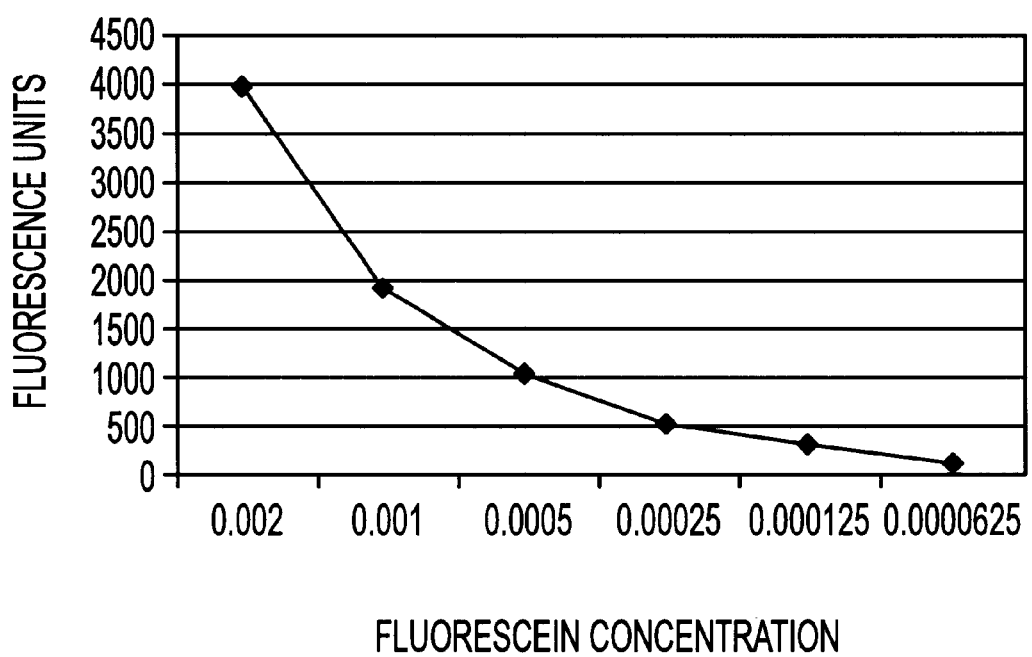
FIG. 2 graphically plots fluorescein units measured on the Cytofluor II fluorometer against the concentration of fluorescein sodium in a sample.

The accuracy of the fluorometer for measuring fluorescein concentration in solution was assessed by measuring fluorescence in a series of serially diluted sodium fluorescein samples (0.002% to $6.25 \times 10^{-5}$%). FIG. 2 shows a comparable decline in the fluorescence with serial dilution.

Fluorescence of tear samples was measured within 24 hours after collection. To confirm that this length of storage did not affect the results, 12 tear fluorescein samples were measured immediately and then again 24 hours after collection. Table 1 shows that there was no change in fluorescence intensity over the 24 hour storage period (Coefficient of Reliability was 1.0, as calculated by the method of Fleiss, Design and Analysis of Clinical Experiments. New York: Wiley, 1982:2–28, the disclosure of which is hereby incorporated herein by reference).

Preferably, sampling of tear fluid fluorescence is performed at 15 minutes after instillation of fluorescein into a patient's inferior conjunctival sac. This preference is based on previous studies showing minimal or no fluorescein remaining in the tear fluid of normal subjects and retention of fluorescein in all subjects with Sjögren's syndrome aqueous tear deficiency at this time point using a Schirmer strip technique (See Pflugfelder et al., *Cornea* 1998: 17:38–56, and Prabhasawat and Tseng, *Br. J. Ophthamology* 1998; 82:666–675; the disclosures of which are hereby incorporated herein by reference).

TABLE 1

Repeated measurement of tear fluorescence

| SAMPLE | 5 MINUTES AFTER COLLECTION | 24 HOURS AFTER COLLECTION |
| --- | --- | --- |
| 1 | 321 | 318 |
| 2 | 222 | 221 |
| 3 | 4325 | 4305 |
| 4 | 3078 | 2987 |
| 5 | 2782 | 2781 |
| 6 | 1792 | 1784 |
| 7 | 428 | 428 |
| 8 | 339 | 330 |
| 9 | 1385 | 1384 |
| 10 | 1628 | 1614 |
| 11 | 12876 | 12548 |
| 12 | 2548 | 2468 |

Coefficient of Reliability=1.0(p=0.13, Paired t-test).

To confirm that 15 minutes was an appropriate time to evaluate tear fluorescein clearance with the more sensitive CytoFluor fluorometer, five ideal normal subjects (ages 20–25 with Schirmer test scores>20 mm) and five patients with Sjögren's syndrome and Schirmer scores<5 mm were evaluated at sequential time points 5 minutes to 60 minutes after instillation of fluorescein. Tear fluorescein concentration approached the detection limits of the CytoFluor in the normal subjects (15.3±8.24 fluorescein units/μl; range 7.1–28.3 fluorescein units/μl) by 15 minutes. By contrast, the mean fluorescence of the samples obtained from the Sjögren's syndrome patients was 5920.6±1407.9 fluorescein units/μl (range 4581–7700 fluorescein units/μl). Beyond the 15-minute time point, tear fluorescence fell below the limits of detection for some of the normal subjects. These findings support the use of a 15-minute sampling time for measuring tear fluorescence with the Cytofluor fluorometer.

Fluorescein clearance and Schirmer test results in patients and control subjects were noted by evaluating the symptoms of ocular irritation and deriving a predictive value for identifying ocular irritation.

The log of tear fluorescein concentration was used for statistical analysis rather than the fluorescein concentration itself because of a three logarithmic unit range of tear fluorescein concentration found in both patients and control subjects. Significantly higher log of tear fluorescence and lower Schirmer test scores were found in patients complaining of ocular irritation than in normal control subjects, as set forth in Table 2.

TABLE 2

Mean of Schirmer 1 Test scores and log tear fluorescein concentration in normal and symptomatic patients.

| SUBJECT GROUP | SCHIRMER SCORE (±SX) | LOG TEAR FLUORESCEIN CONCENTRATION ±SD)[1] |
| --- | --- | --- |
| NORMAL (Asymptomatic) (n = 40) | 22.25 ± 8.27 mm | 1.89 ± 0.70 |

TABLE 2-continued

Mean of Schirmer 1 Test scores and log tear fluorescein concentration in normal and symptomatic patients.

| SUBJECT GROUP | SCHIRMER SCORE (±SX) | LOG TEAR FLUORESCEIN CONCENTRATION ±SD)[1] |
|---|---|---|
| AB-NORMAL Symptomatic | 12.5 ± 8.84 mm[2] | 3.07 ± 0.61[3] |

[1]Tear fluorescent units measured 15 minutes after instillation of fluorescein as described in methods.
[2]P > 0.0005; normal vs. symptomatic, two sample 1-test.
[3]P > 0.0005; normal vs. symptomatic, two sample 1-test.
(SD) = Standard deviation.

Figure 3:
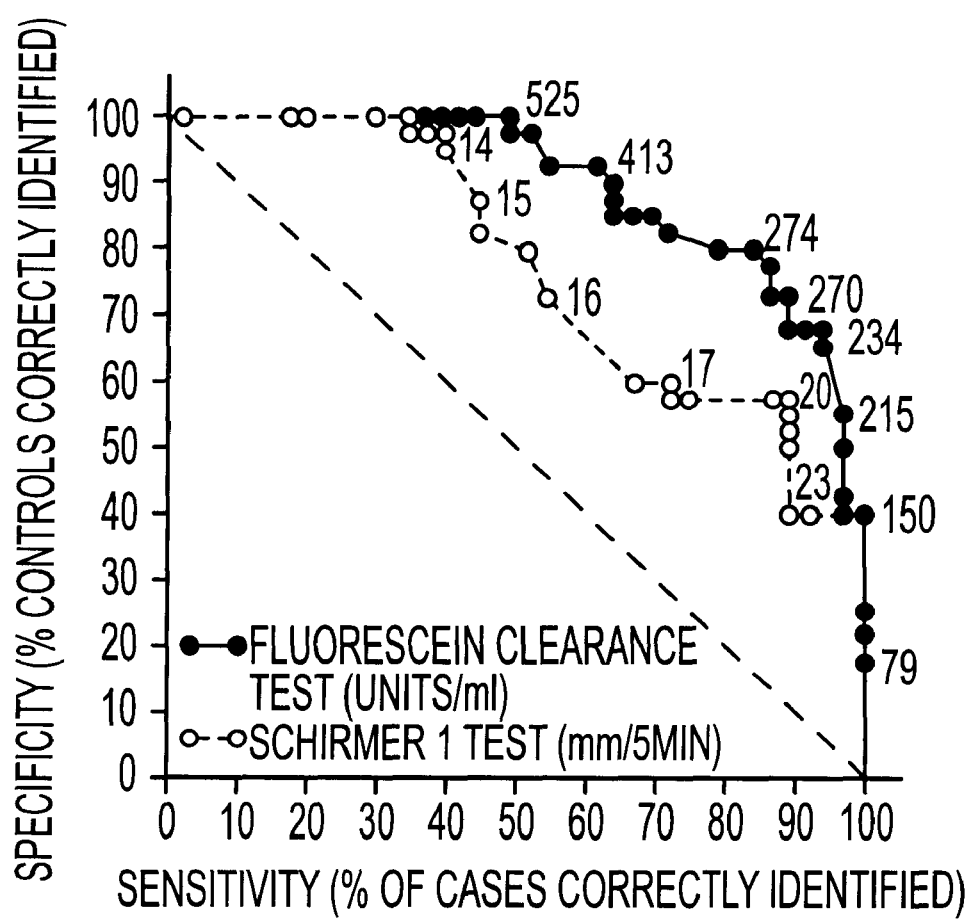
FIG. 3 graphically depicts receiver operating characteristic curves for the fluorescein clearance test and the Schirmer 1 test.

Irritation symptoms correlated with higher log tear fluorescein concentration (symptomatic 3.08+/−0.62 units/$\mu$l, normal control 1.89+/−0.7 units/$\mu$l, p<0.005) and lower Schirmer 1 test scores (symptomatic 12.6 mm, normal control 22.3 mm. p<0.005). The fluorescein clearance test showed greater predictive value for identifying ocular irritation than the Schirmer 1 test. FIG. 3 displays a receiver operating characteristic curve (See McNeil et al., *N. Engl. J. Med.* 1975; 293:211–215, the disclosure of which is hereby incorporated herein by reference), which contrasts the sensitivity and specificity of both the Schirmer 1 and fluorescein clearance tests. The receiver operating characteristic graph displays one curve for fluorescein clearance (dark circles) and one curve for the Schirmer test (open circles). The numbers to the right of each curve indicate the cutoff values for various combinations of sensitivity and specificity for each test. For the fluorescein clearance graph, the numbers are fluorescent units per $\mu$l and for the Schirmer test are millimeters of strip wetting. The curve the farthest from the 1:1 line (dashed line) indicates the test with the best ability to discriminate between cases and controls.

Notably, the fluorescein clearance curve is located further from the 1:1 line (dashed line) than the Schirmer 1 curve. This indicates that the fluorescein clearance test has a higher sensitivity for identifying cases of ocular irritation for specificities ranging from 40 to 100 percent. Additional logistic regression analyses demonstrated that the fluorescein clearance test was also statistically better than the Schirmer test in discriminating between ocular irritation patients and control subjects (p<0.001). A tear fluorescein concentration of 274 units/$\mu$l at 15 minutes eliminated 80% of the normal subjects (specificity) and identified 85% of the abnormal patients (sensitivity), while a fluorescein concentration of 525 units/$\mu$l had 100% specificity for ocular irritation symptoms. The points on these curves represent possibilities associated with designating a subject with a given value of each test as having ocular irritation associated with a tear film disorder. Although derived from the data, the points do not correspond to values for the patients in the study.

Figure 4A:
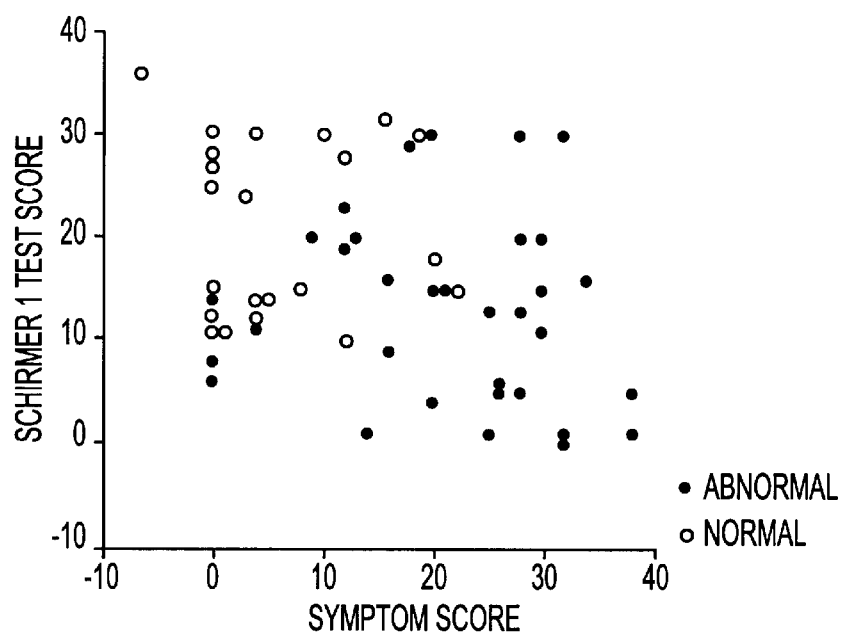
FIG. 4a shows symptom severity scores versus Schirmer 1 test scores, correlated by the statistical parameters of Spearman's rho=−0.39, p<0.001.
Figure 4B:
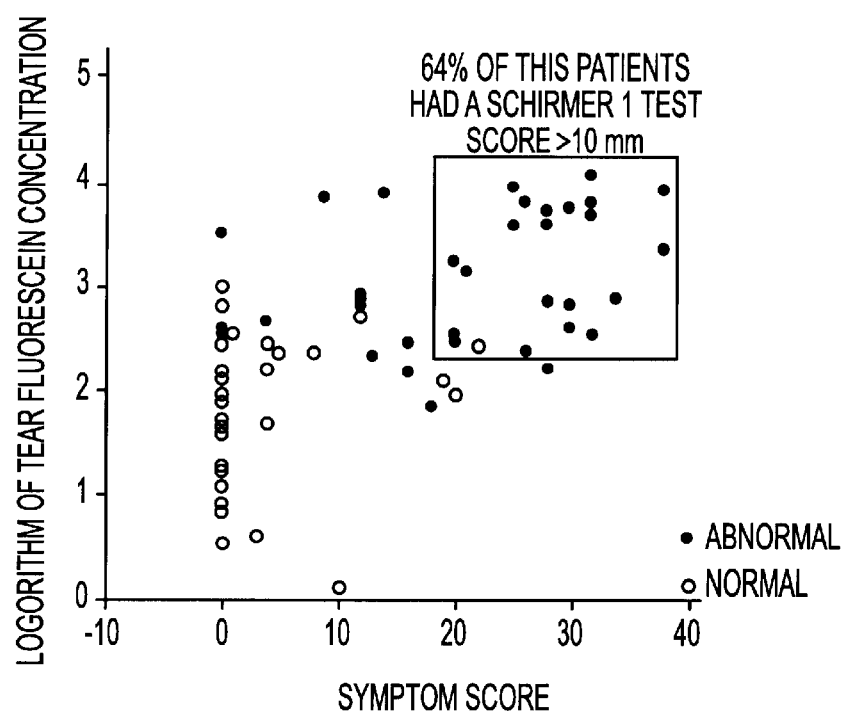
FIG. 4b shows symptom severity scores versus log tear fluorescein concentration, correlated by the statistical parameters of Spearman's rho=0.65, p<0.001.
Figure 5:
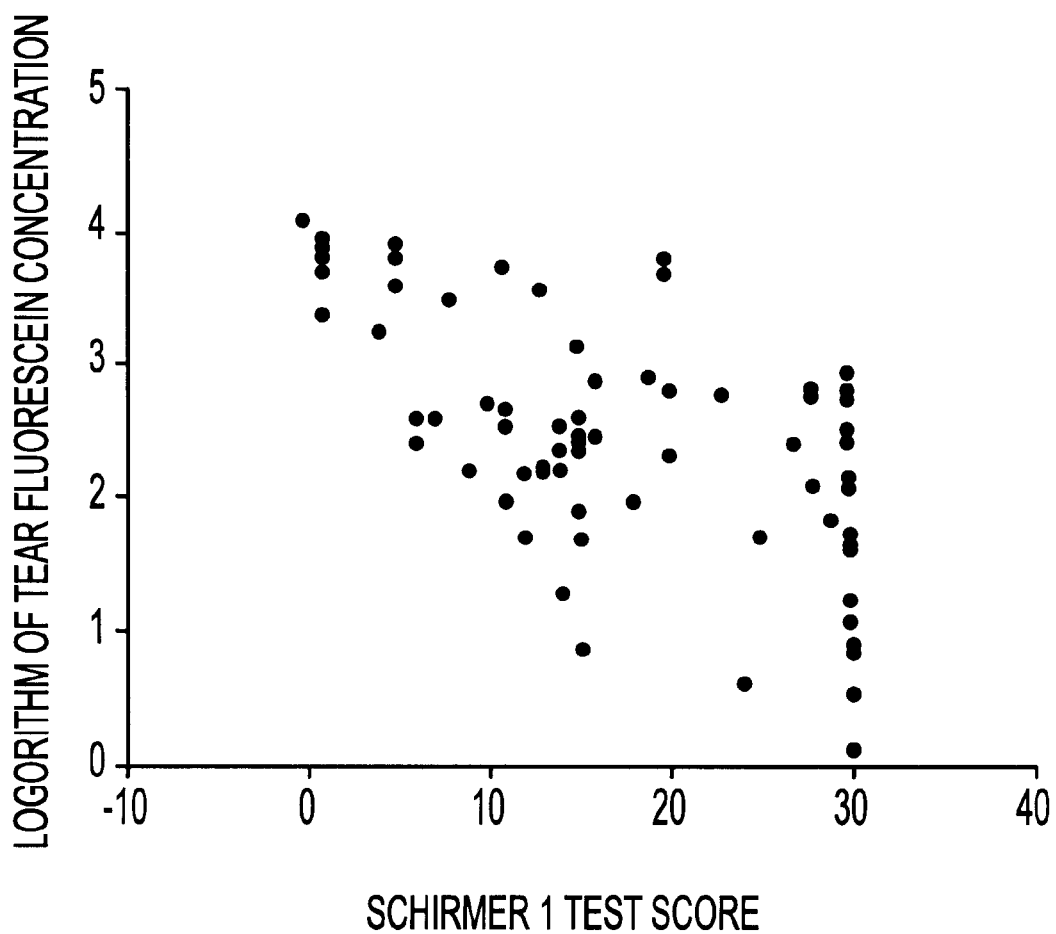
FIG. 5 correlates log tear fluorescein concentration with Schirmer 1 test, correlated by the statistical parameters of scores r=−0.585, p<0.001.

An inverse correlation was noted between symptom severity and Schirmer 1 test scores (FIG. 4a, Spearman's rho=−0.39, p<0.001). Despite this correlation, a wide range of Schirmer scores (1 mm to 30 mm) was noted in patients with high symptom severity scores. A greater delay in tear fluorescein clearance (indicated by a greater tear fluorescein concentration) was observed as irritation symptoms worsened (FIG. 4b). The observed delay in tear fluorescein clearance may have been due in part to the correlation between fluorescein clearance and the Schirmer test. As seen in FIG. 5, tear fluorescein concentration increased as aqueous tear production measured by the Schirmer test decreased. Nevertheless, 64% of abnormal subjects with a symptom severity score>18 and log fluorescein concentration>2.4 (designated in the box on FIG. 4b) had Schirmer scores>10 mm. This finding suggests that reduced aqueous tear production is not the only factor responsible for delayed tear clearance in patients with ocular irritation.

Meibomian gland disease percent acinar drop-out and orifice metaplasia were determined for comparing Schirmer test and fluorescein clearance. Table 3 shows that as the percentage of meibomian gland acinar drop-out increased, tear fluorescein concentration increased (p<0.001, analysis of variance) and Schirmer 1 test scores decreased (p<0.001, analysis of variance). Further analysis demonstrated that fluorescein clearance was different for each of the three levels of acinar drop-out, while no difference in Schirmer 1 test scores was observed between the 34–66% and 66–100% acinar drop-out groups (post-hoc least significant test). The presence of orifice metaplasia was significantly correlated with fluorescein clearance and Schirmer test scores (p<0.001, two-sample 1-test, Table 3).

TABLE 3

Association between log tear fluorescein concentration and Schirmer test scores and Meibomian Gland Disease.

| PERCENT MG ACINAR LOSS | MEAN (± SD) OF SCHIRMER TEST SCORES | MEAN (±SD) OF TEAR FLUORESCEIN CONCENTRATION[1] |
|---|---|---|
| 0–33% | 23.92 ± 7.58 MM | 1.86 ± 0.78 |
| 34–66% | 15.50 ± 8.52 mm | 2.50 ± 0.73 |
| 67–100% | 13.04 ± 10.16 mm (*) | 3.07 ± 0.75(\) |
| Presence of MG orifice metaplasia. | | |
| Metaplasia | 14.47 ± 8.53 mm | 2.81 ± 0.78 |
| No Metaplasia | 23.14 ± 7.67 mm(‡) | 1.83 ± 0.71(§) |

MG = Meibomian gland,
SD = Standard deviation.
[1]Fluorescence units.
(*) P > 0.001, 0–66% vs. 67–100% of acinar loss, one wall analysis of variance.
(†) P > 0.001, 0–66% vs. 67–100% of acinar loss, one way analysis of variance.
(‡) P > 0.001, metaplasia vs. no-metaplasia, two sample t-test.
(§) P > 0.001, metaplasia vs. no-metaplasia, two sample t-test.

Log of tear fluorescein concentration and the Schirmer 1 test correlated with meibomian gland orifice metaplasia (2.81+/−0.78 units/$\mu$l and 14.47+/−9.53 mm in those with metaplasia vs. 1.83+/−0.71 units/$\mu$l and 23.14+/−7.67 mm in those without metaplasia, p<0.001) and with the percentage of acinar drop-out.

No statistical difference in age was noted between groups (the mean age of the normal controls was 53±22 years and the symptomatic patient was 56±17 years; p=0.4, two-sample t-test). A small, but statistically significant, increase in log of tear fluorescein concentration was associated with aging (p=0.033, slope=0.1 log unit increase per decade of age by least squares linear regression). In contrast, Schirmer test scores were not found to correlate with age (p=0.2, least squares regression).

Figure 6:
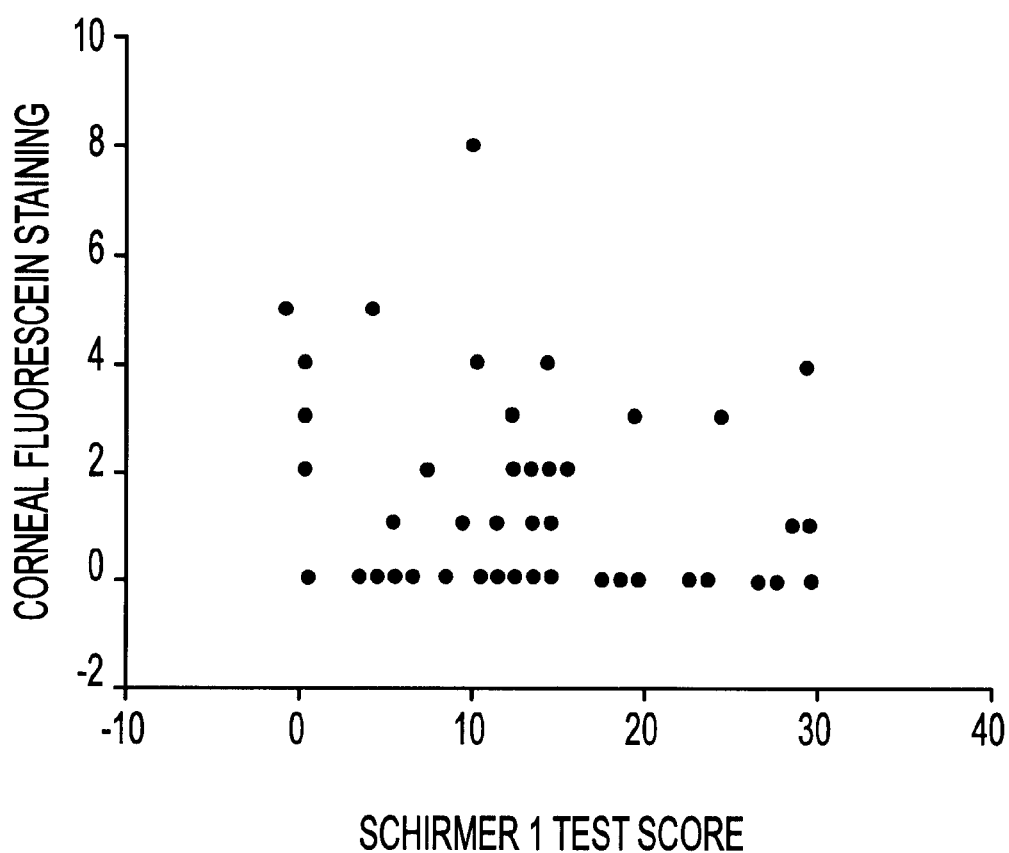
FIG. 6 shows Schirmer 1 test scores and corneal fluorescein staining, correlated by the statistical parameters of Spearman's rho=−0.39, p<0.001.
Figure 7:
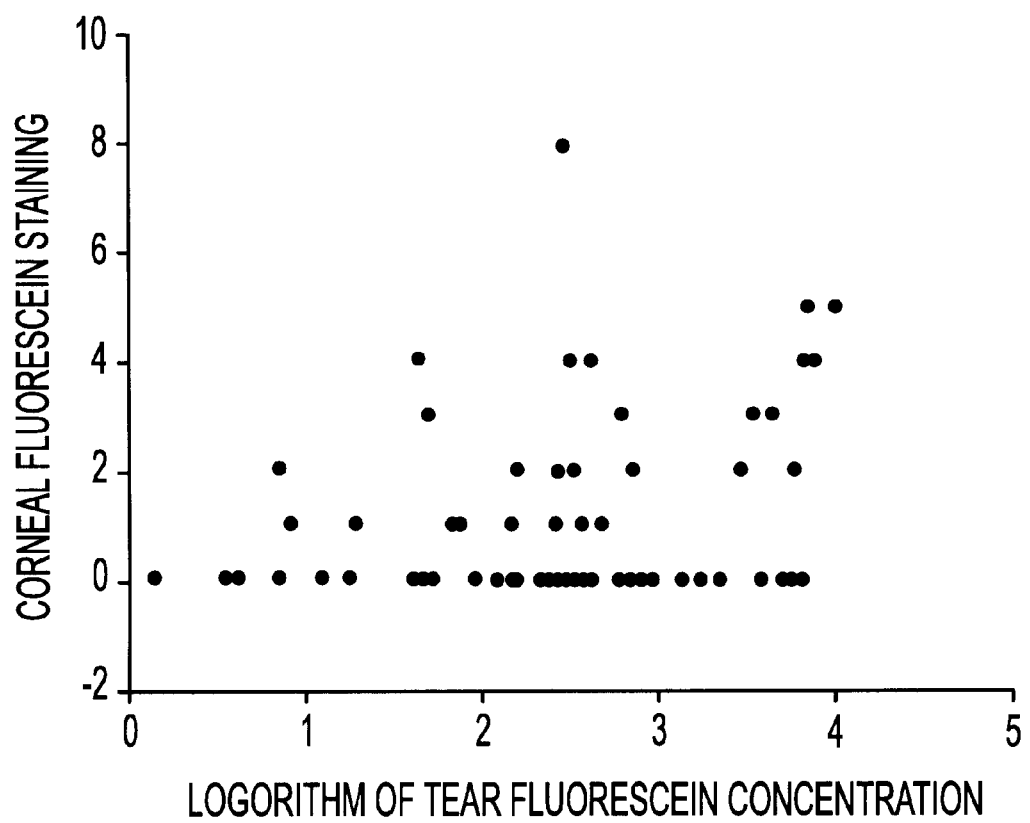
FIG. 7 graphically depicts log tear fluorescein concentration and corneal fluorescein staining, correlated by the statistical parameters of Spearman's rho=0.263, p<0.018.
Figure 8:
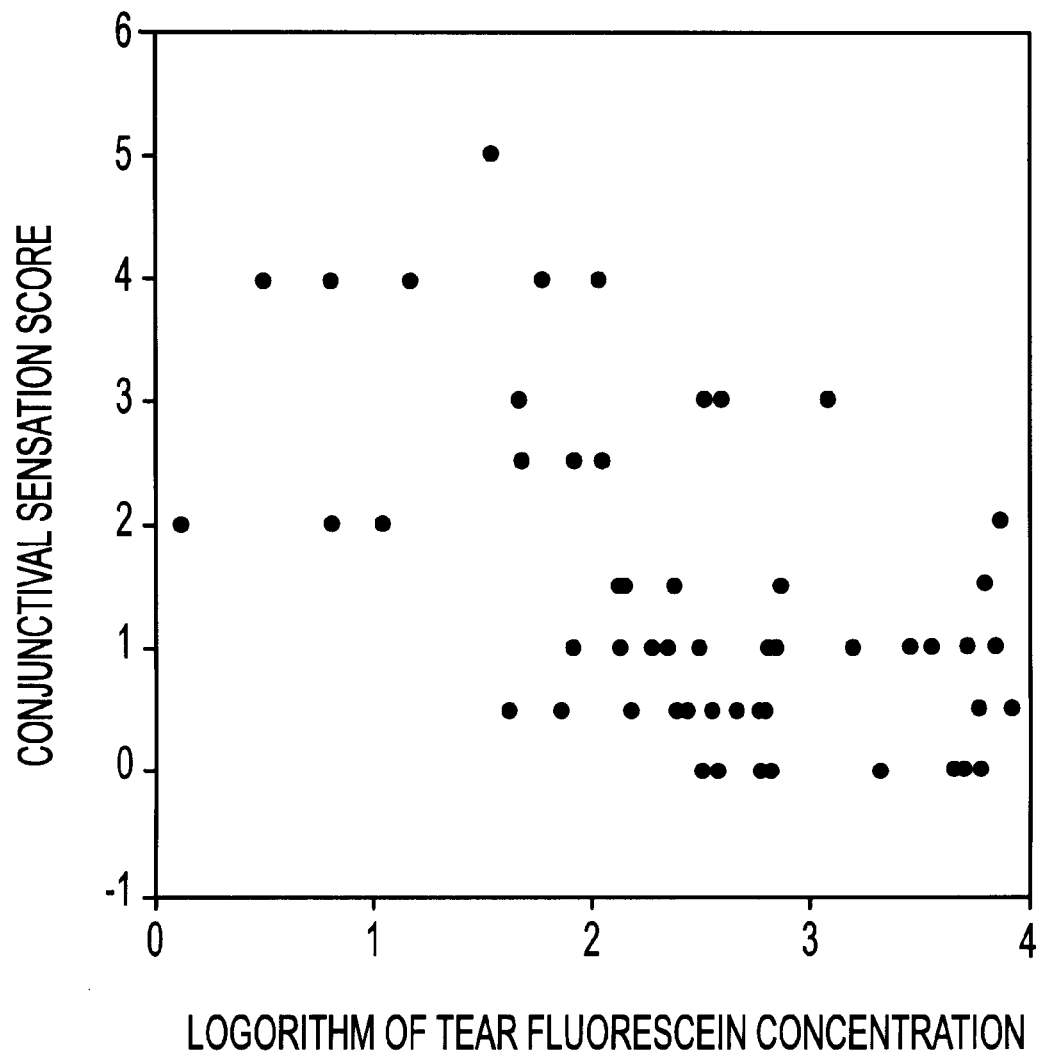
FIG. 8 graphically depicts log tear fluorescein concentration and conjunctival sensation score measured with the Cachet Bonnet anesthesiometer, correlated by the statistical parameters of Spearman's rho=−0.391, p=0.001.

Both log of tear fluorescein concentration and the Schirmer 1 test correlated with corneal fluorescein staining (Pearson Correlation of 0.394 p<0.0001 for Schirmer 1 test, and 0.312 p<0.005 for log of tear fluorescein). Corneal fluorescein staining scores showed greater correlation with Schirmer test scores (Spearman's rho=−0.39, p<0.001) than with log tear fluorescein concentration (Spearman's rho= 0.263, p=0.018) (FIGS. 6 and 7). Corneal sensitivity scores correlated with both reduced tear fluorescein clearance (Spearman's rho=−0.38, p=0.003) and reduced Schirmer test scores (rho=0.39, p=0.002). A correlation was also found between fluorescein clearance and conjunctival sensation (rho=−0.391, p=0.001, FIG. 8). Conjunctival sensation showed less correlation with Schirmer test scores (rho=0.23, p=0.061)

The fluorescein clearance test according to the invention shows a greater predictive value for ocular irritation than the Schirmer 1 test. The invention correlates better with age, meibomian gland dysfunction, and decreased corneal and conjunctival sensation. Decreased tear clearance was identified as a risk factor for ocular irritation even in subjects with normal Schirmer scores. This simple technique may provide new clues into the mechanism and therapy of ocular irritation.

Delayed fluorescein clearance is expected in patients having aqueous tear deficiency because of reduced tear volume and tear flow rate. Indeed, the results presented herein show that tear fluorescein concentration increases as the Schirmer test score decreases. One interesting finding confirming previous reports of the inventors is that fluorescein clearance is also delayed in some "Schirmer normal" (>10 mm wetting) patients with complaints of ocular irritation (FIG. 4b). This corroborates previous findings (See Pflugfelder, et al., supra) that delayed tear clearance, independent of the level of aqueous tear production, shows statistically significant correlation with ocular irritation symptoms. These results also suggest that in addition to the Schirmer test, the fluorescein clearance test is a clinically useful diagnostic test for evaluating patients complaining of ocular irritation. Unlike the Schirmer test, tear fluorescein clearance was found to decrease with age, confirming previous observations by the inventors in a different patient population (See Nava, et al., supra). Aging changes of the eye and ocular adnexae such as conjunctivochalasis, lid laxity, functional tear outflow obstruction and blink abnormalities may all contribute to the observed reduction in tear fluorescein clearance and the irritation symptoms that accompany such a reduction.

Similar to previous reports, the process according to the invention revealed the presence of meibomian gland pathology in some asymptomatic patients, but overall the severity of meibomian gland disease was found to correlate with the severity of irritation symptoms. Both reduced Schirmer test scores and delayed tear clearance were found to be associated with meibomian gland disease. Therefore, irritation symptoms in patients with meibomian gland disease may be exacerbated by reduced tear production or delayed fluorescein clearance, or both. One mechanism by which delayed tear fluorescein clearance may induce irritation symptoms is by increasing ocular surface inflammation. Recent work indicates that patients with ocular rosacea and meibomian gland disease show increasing concentrations of the pro-inflammatory cytokine, interleukin-1 alpha (IL-1α) as tear fluorescein clearance decreased (See Barton K, Monroy D C, Nava A, Pflugfelder S C. *Ophthalmology* 1997; 104:1868–74). Additional evidence supporting the association of inflammation with irritation symptoms is that treatment of patients with delayed tear clearance with a topical non-preserved corticosteroid reduced irritation symptoms and objective signs (redness and dye staining) in 80% of patients and improved tear clearance in 87%. Future studies are warranted to further the causal relationship between delayed tear clearance, inflammation and ocular irritation.

Both Schirmer and fluorescein clearance tests were strongly correlated with total corneal fluorescein staining scores. It is well recognized that ocular surface dye staining in patients with aqueous tear deficiency occurs in an exposure zone pattern. Patients with delayed fluorescein clearance and lipid deficiency as a result of meibomian gland disease exhibit ocular surface dye staining which is less severe than is associated with aqueous tear deficiency, tending to occur in a non-exposure zone pattern. Perhaps the mechanism of dye staining occurring in patients with delayed tear clearance and nominal aqueous tear production is different from that observed in aqueous tear deficiency. Additional studies will be required to confirm this theory.

The concentration of topically applied medications and their preservatives will be increased in patients with delayed tear clearance compared to individuals with normal clearance. Patients with delayed tear clearance reportedly have an increased risk for developing ocular surface medication toxicity, such as drug-induced pseudopemphigoid, conjunctival redness and punctate keratopathy. Frequent application of eye drops containing toxic preservatives, such as benzalkonium chloride, should be used with caution in patients with delayed clearance to avoid further damage to an already compromised ocular surface.

Patients with dry eye historically have reduced corneal sensitivity scores. According to the inventive method, reduced aqueous tear production is correlated with reduced corneal sensation. However, delayed tear fluorescein clearance is correlated with reduced corneal and conjunctival sensation.

One implication of reduced ocular surface sensation is a reduction in blink rate that may further decrease tear clearance. The finding of reduced sensation is paradoxical, given the fact that reduced clearance strongly correlated with irritation symptoms. One explanation for this paradox is that the sensory receptors tested by the anesthesiometer used in the present study are different than the ones responsible for causing irritation symptoms.

The majority of aqueous tear production by the lacrimal glands is driven by sensory neural stimulation from the trigeminal nerves innervating the ocular surface, adnexae and nasal mucosa. Therefore, the reduced ocular surface sensation found in patients complaining of ocular irritation may create a vicious cycle of reduced aqueous tear secretion leading to greater delay in tear clearance, further decrease in ocular surface sensation and worsening irritation symptoms. This may be complicated by the fact that pro-inflammatory cytokines, such as interleukin type 1α, and the matrix degrading enzymes, such as matrix metalloproteinase 9, increase in concentration in tear fluid of patients with dry eye.

These findings indicate that tear fluorescein clearance test is a better diagnostic test than traditional tests used to identify the underlying causes of eye irritation complaints or corneal epithelial disease in patients with tear film problems. The invention is an addition to the diagnostic armamentarium for ocular irritation, providing a source of future therapeutic strategies for dry eye.

Example II

In another embodiment, the invention provides a diagnostic kit for measuring tear clearance. The diagnostic kit for measuring tear clearance may comprise an indicator suitable for introduction into an inferior conjunctival sac of an eye, the indicator comprising a member selected from the group consisting of a dye, an enzyme and a chemical. The indicator may be directly visualizedin the inferiro tear meniscus or through a subsequent chemcial reaction producing an visually detectable product. The kit would also comprise a color standard for measuring indicator present in the inferior meniscus of a treated eye between about 5 and about 15 minutes after introduction of the indicator to the eye.

Another embodiment of a diagnostic kit for measuring tear clearance according to the invention may comprise:

(a) a fluorescein dye solution suitable for introduction into the inferior conjunctival sac of an eye;

(b) optionally, a substrate for collecting a sample of tear fluid from the eye; and (c) a color standard for measuring the amount of fluorescence present in the tear fluid.

Figure 9:
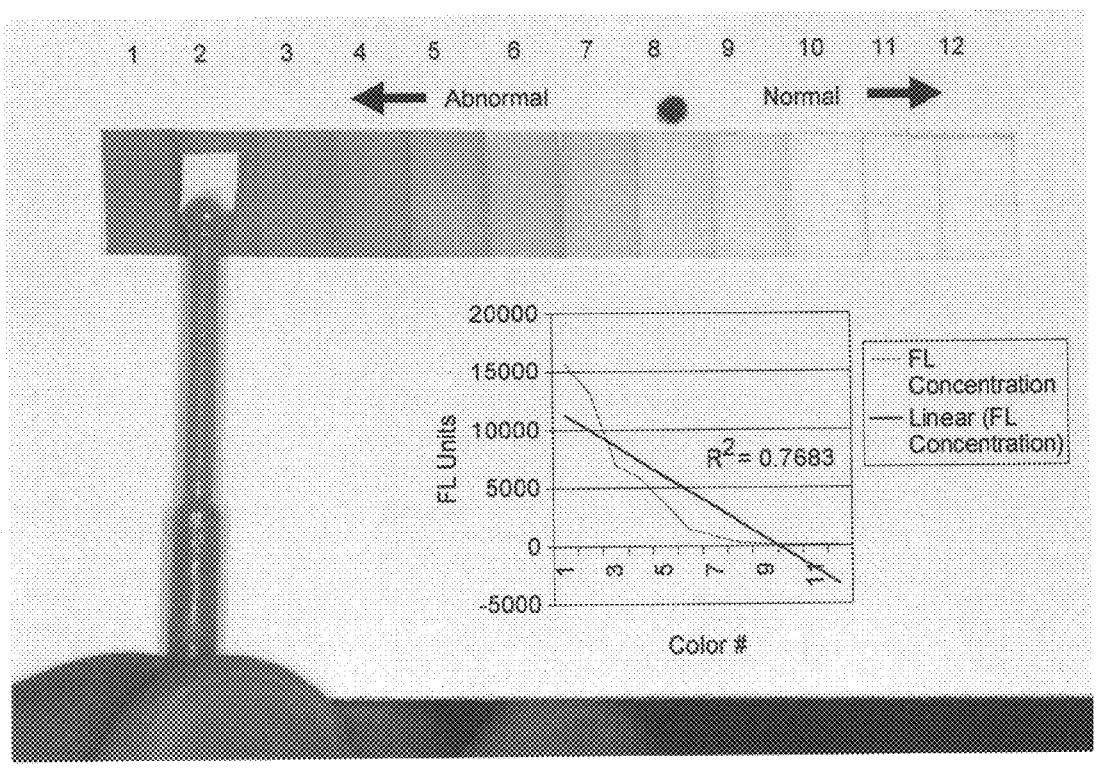
FIG. 9 shows a fluorescein standard color plate and the relationship of fluorescein concentration versus detectable color.

The diagnostic kit according to invention may comprise a unit-dose dropperette for introducing or administering fluorescein dye solution is introduced to the eye of a mammalian patient. In such a diagnostic kit, the unit-dose dropperette administers dosages of about 0.5 microliters to about 5 microliters of fluorescein dye solution to the patient's eye, preferably to the conjunctival sac. Assessment of tear fluorescein concentration may be performed by collecting small volumes of tear fluid, between, for example, 0.5 $\mu l$ to 3 $\mu l$, on a substrate, such as a filter paper strip, polyester wick or the like, and comparing the color of the fluorescein-stained substrate to color standards. The color standards may be in the form of a color photographic plate, as is shown in FIG. 9. Alternatively, the color of fluorescein in the inferior tear meniscus may be visually compared to a color standard using a biomicroscope. Under these conditions, the kit would contain a color standard plate of appropriate size for placement along the lower eyelid to be viewed under a biomicroscope simultaneously with the inferior tear meniscus. The advantages of such kits include low cost per test and an easily administered test for diagnosing delayed tear clearance as the causation of ocular irritation and/or ocular surface diseases. Clinicians would be able to administer such tests in settings outside the hospital, such as in clinics and vision centers, making the technology and its benefits available to large numbers of patients.

Example III

In this embodiment of the invention, correlations are made between the Fluorescein Clearance Test (FCT) and the Schirmer test with the severity of corneal epithelial and eyelid disease in normal subjects and patients with tear film disorders due to meibomian gland disease (MGD) and/or aqueous tear deficiency (ATD).

Research to evaluate the above-mentioned test parameters was conducted by medically qualified personnel in strict accordance with the guidelines of the University of Miami School of Medicine Institutional Review Board and in accordance with the Tenets of the Declaration of Helsinki.

The enrolled patients had no history of the following: ocular surgery, contact lens use, punctal occlusion or use of eye drops use (other than non-preserved artificial tears) for at least one month. Subjects did not instill any tear drops in their eyes on the day they were evaluated. Adult patients presenting with complaints of ocular irritation were evaluated by the inventors at the Ocular Surface Center (Bascom Palmer Eye Institute—University of Miami School of Medicine). Each subject was first asked to complete a symptom questionnaire consisting of 11 questions describing the severity and the nature of their irritation symptoms (Table 4). Table 4—Symptom questionnaire (score ranging from 0 to 48). In sections A and C: the score for each row ranged from 0 to 4. In section B the score for each row ranged from 0 to 6.

TABLE 4

Symptom questionnaire (score ranging from 0 to 48). In sections A and C: the score for each row ranged from 0 to 4. In section B the score for each row ranged from 0 to 6.

| A | None of The time | Some of the time | Half of the time | Most of the time | All of the time |
|---|---|---|---|---|---|

Have you experienced any of the following during the last week:

1 light sensitivity
2 Gritty or scratchy sensation
3 Burning or stinging
4 Vision that fluctuates with blinking
5 Vision that improves with artificial tears
6 Tearing
7 Pain or burning in the middle of the night or upon awakening in the morning

| B | None of the time | Seldom the time | Some of the time | Half of the time | Most of the time | Almost all of the time | Always |
|---|---|---|---|---|---|---|---|

Have problems with your eyes limited you in performing any of the following during the last week:

8 Reading or driving a car for a long period
9 Watching TV or working on a computer for an extended period

| C | None of the time | Some of the time | Half of the time | Most of the time | All of the time |
|---|---|---|---|---|---|

Have your eyes felt uncomfortable in any of the following situations during the last week:

10 Windy conditions
11 Places with low humidity such as air conditioned or heated buildings or airplanes Patients then underwent a panel of diagnostic tests performed in the following order: corneal and conjunctiva sensation, fluorescein clearance test, corneal fluorescein staining, Schirmer 1 test, and biomicroscopic examination of the eyelid margins and meibomian glands. Patients were classified into one of three groups based on the following inclusion criteria.

Patients determined to have aqueous tear deficiency had a Schirmer 1 test<5 mm in at least one eye and a symptom questionnaire score>5.

Patients determined to have meibomian gland disease had a Schirmer 1 test>5 mm in both eyes and a symptom questionnaire score>5. They were classified as having rosacea associated (inflammatory) MGD or non-inflammatory meibomian gland atrophy. Diagnosis of rosacea was based on previously reported criteria and required the presence of at least two facial signs of rosacea (which include rhinophyma, telengiectasia, persistent erythema, papules, pustules, and hypertrophic sebaceous glands in facial flush areas) and hyperemia of lid margins (brush marks) and/or conjunctival hyperemia. Atrophic MGD was defined as at least 30% atrophy of meibomian gland acini in lower lid (determined by transillumination of lower lid as described below), no facial signs of rosacea, and mild or no hyperemia of the lid margins or conjunctiva.

A group of 19 normal subjects of similar age and gender distribution was evaluated as a control group. Subjects were considered normal if they had no history of ocular irritation (symptom questionnaire score<5), no use of eyedrops, and had a Schirmer 1 test score>10 mm in both eyes.

The Fluorescein-Clearance Test was performed with a CytoFluor II fluorophotometer by measuring the fluorescein concentration in minimally stimulated tear samples collected from the inferior tear meniscus 15 minutes after instillation of 5 $\mu$l of 2% sodium fluorescein as previously reported (See Afonso, et al., supra).

The ocular surface of patient eyeballs was examined with a biomicroscope and the x10 objective under blue-light illumination two minutes after fluorescein instillation into the tear film. Density of corneal fluorescein staining was assessed using techniques known in the art in each of four quadrants on the cornea: temporal, nasal, superior and inferior using a 4 point standardized scale (0=none; 1=mild; 2=moderate; 3=severe). The range of staining scores was from 0 to 12.

Without previously instilling anesthetic drops, Schirmer paper test strips (Alcon Laboratories, Inc. Fort Worth, Tex.) were placed over the lid margin at the junction of the lateral and middle thirds of the lower eyelid for 5 minutes. The length of strip wetting in millimeters was recorded.

Cornea and conjunctiva sensation were assessed by using the Cochet-Bonnet esthesiometer. The stimulus from the Cochet Bonnet consists of a nylon filament that can be varied in length from 0 cm to 6 cm. The procedure for measuring ocular surface sensitivity was performed as follows: under visual control, the nylon filament of the Cochet Bonnet instrument was approached smoothly and perpendicularly toward the center of the cornea. Contact was detected by the slightest bend of the nylon; sensitivity was taken as the length of the filament that gave a 50% positive response from a minimum of four stimulus applications. Subject reliability was tested by bringing the filament close to the cornea without actually making contact therewith. The same procedure was used to test conjunctival sensation with the stimulus applied to the middle of the exposed temporal-bulbar conjunctiva.

The meibomian gland orifices were examined by slit-lamp biomicroscopy for the presence of metaplasia, characterized by abnormal growth and keratinization of duct epithelium manifesting as white shaft protruding from the orifices. The inferior tarsus was transilluminated with a halogen Finhoff transilluminator (Welch Allyn, Inc., Schenectady, N.Y., U.S.A.) and the percentage of meibomian gland acinar dropout was measured as previously reported (See Pflugfelder and Tseng, *Cornea,* 1998; 17:38–56, the disclosure of which is hereby incorporated herein by reference).

The presence of irregularity of the lid margin and of anterior migration of Marx's line was evaluated by slit-lamp biomicroscopy. Anterior migration of Marx line was determined using previously published criteria (See Norn, *Acta Ophthalmol* (*Copenh*) 1985; 63: 698–700, the disclosure of which is hereby incorporated herein by reference).

For statistical evaluation, only the right eye was considered for each patient. Data distribution was analyzed. If data were normally distributed, then parametric statistical tests were used, otherwise non-parametric tests were utilized. The differences in age among the three groups (normal controls, patients with meibomian gland disease and patients with aqueous tear deficiency) were studied by means of one-way analysis of variance and Bartlett's test for equal variances. The difference in gender among the three groups was studied using the Kruskal Wallis Statistic.

Correlation coefficients were calculated between the fluorescein clearance test and Schirmer 1 test, corneal fluorescein staining score, anterior migration of Marx line, percentage of Meibomian gland acinar loss, presence of orifice metaplasia (0=absent, 1=present) and cornea and conjunctiva sensitivity scores. If data distribution was normal, then the Pearson correlation coefficient was used; otherwise the Spearman rank correlation coefficient was calculated. Furthermore, the correlation coefficients between symptom questionnaire score and fluorescein clearance test, Schirmer test and corneal fluorescein staining scores were evaluated for each group of patients (MGD, ATD and normal controls).

The following equation, correction formula I, was used to correct the results of the FCT by the Schirmer test:

$$FCT(\text{corrected}) = FCT + \text{Schirmer score.}(y) \quad \text{I}$$

The coefficient y was calculated by looking for the best corresponding area under the Receiver Operating Characteristic (ROC) curves according to methods known in the art (See Buvat et al., *J. Nucl. Med* 1998; 39:1590–1596, the disclosure of which is hereby incorporated herein by reference).

All statistical calculations were performed with GraphPad Prism 2.0 Software.

No significant differences in age and gender were found between normal control subjects (average age±SD= 59.4±15.4 years), patients with MGD (average age= 59.7±17.5 years) and patients with ATD (average age= 66.3±16.2 years); for age, a one-way analysis of variance was used (P=0.2), Bartlett's statistic (corrected) (P=0.8); for gender, the Kruskal Wallis Statistic was used (P=0.7).

Sixteen of the MGD patients had rosacea and twenty-one had non-inflammatory atrophic disease. There was no statistical difference in age (Mann Whitney U test, P=0.2) and in gender (Mann Whitney U test, P=0.7) between these two groups. The two groups of MGD patients were combined for statistical analysis.

The mean and the standard deviation values of diagnostic tests for the 3 studied groups are provided in Table 5, and the significant differences among them are noted.

The best value for y in the FCT corrected by the Schirmer test score was found to be 4. Thus, the formula that provided the best area under the ROC curves was:

$$FCT(\text{corrected}) = FCT + \text{Schirmer score.} \quad (4)$$

The differences in FCT corrected among the three groups was found to be statistically significant (Kruskal Wallis statistic=30.2, P<0.0001), and also the differences in FCT corrected between MGD and ATD patients were statistically significant (Mann Whitney U=474, P<0.0001) as shown in Table 5.

mian gland orifice metaplasia, percentage of meibomian gland acinar dropout) and cornea and conjunctiva sensitivity scores are presented in Table 7.

Table 8 and FIGS. 12–18 present the correlations between corneal fluorescein staining scores and the Schirmer 1 test, the FCT and the FCT corrected by Schirmer 1 test for MGD patients, ATD patients and all subjects.

The study evaluated the correlations of the Fluorescein Clearance Test (FCT) and the Schirmer test with the severity of corneal epithelial and eyelid disease in normal subjects

TABLE 5

Statistical comparison of three groups [Normal control subjects, Meibomian Gland Disease (MGD) and Aqueous Tear Deficiency (ATD) patients].

| Group | Corneal fluorescein Staining score | Schirmer 1 test (mm.) | % Meibomian Gland Atrophy | Meibomian Gland Orifice Metaplasia | Fluorescein Clearance Test (fluorophotometric units/µl) | Corrected Fluorescein Clearance Test | Corneal Sensation | Conjunctival Sensation |
|---|---|---|---|---|---|---|---|---|
| Normal controls (n = 19) | 0.0 ± 0.0 | 21.7 ± 5.1 | 2.6 ± 11.5 | 0.1 ± 0.2 | 95.4 ± 80.4 | 182.1 ± 68.5 | 5.7 ± 0.2 | 3.4 ± 0.6 |
| MGD (n = 37) | 1.9 ± 2.3 | 17.0 ± 7.5 | 62.6 ± 27.8 | 0.9 ± 0.4 | 520.3 ± 1356.2 | 666.3 ± 1350.2 | 4.2 ± 1.4 | 1.3 ± 0.8 |
| Differences Between Normals and MGD | — | t = 2.4 P = 0.02 | U = 38.0 P < 0.0001 | U = 65.5 P < 0.0001 | U = 280.5 P = 0.22 | U = 274.0 P = 0.18 | U = 94.0 P < 0.0001 | U = 19.0 P < 0.0001 |
| ATD (n = 43) | 2.6 ± 3.0 | 1.8 ± 1.7 | 33.7 ± 33.3 | 0.5 ± 0.4 | 1329.8 ± 2348.2 | 1446.9 ± 2412.0 | 3.7 ± 1.6 | 0.9 ± 0.6 |
| Differences Between MGD and ATD | U = 669.5 P = 0.22 | t = 12.9 P < 0.0001 | U = 286.0 P < 0.0001 | U = 485.5 P = 0.002 | U = 380.5 P < 0.0001 | U = 524.0 P = 0.008 | t = 1.25 P = 0.21 | t = 2.0 P = 0.048 |
| Differences Among the 3 groups | K = 6.5 P = 0.038 | F = 131.1 P < 0.0001 | K = 48.1 P < 0.0001 | K = 34.4 P < 0.0001 | K = 30.2 P < 0.0001 | K = 20.8 P < 0.0001 | K = 29.5 P < 0.0001 | K = 43.0 P < 0.0001 |

Average ± standard deviation.
U = Mann Whitney U test.
t = two tailed unpaired t test.
K = Kruskal Wallis statistic.
F = One-way analysis of variance.

Figure 10:
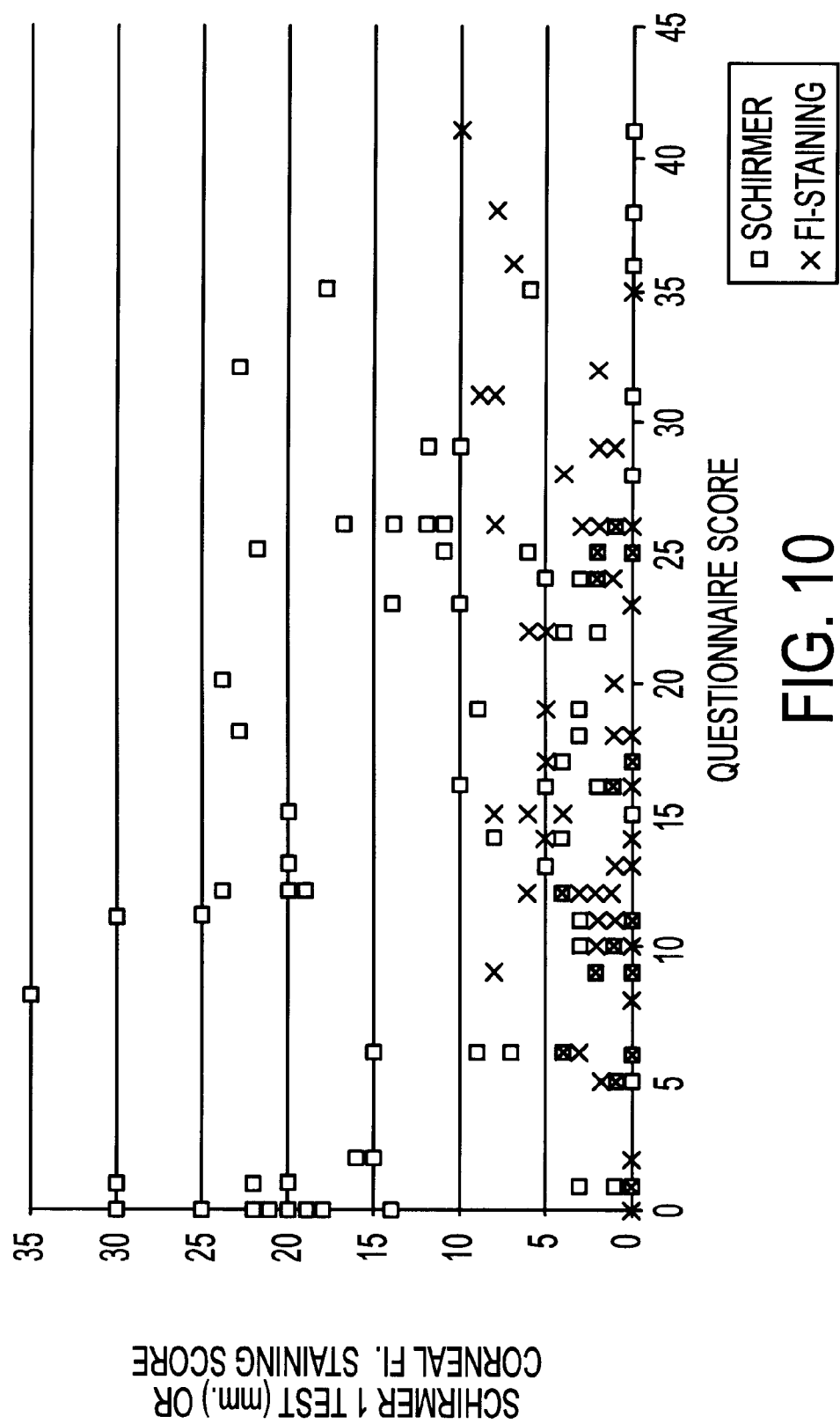
FIG. 10 graphically shows Schirmer 1 test scores or fluorescein staining scores correlated with patient questionnaire scores.
Figure 11:
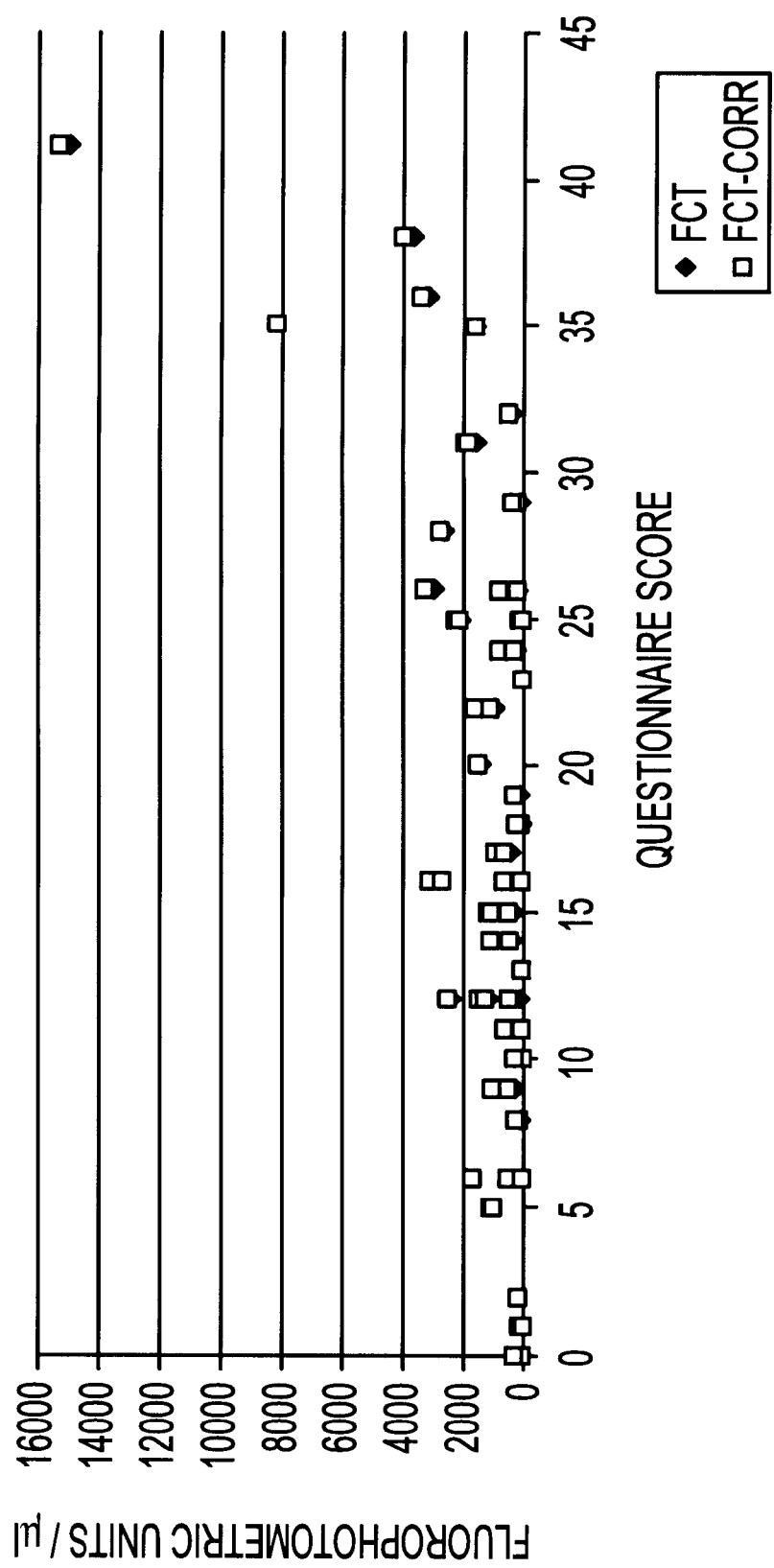
FIG. 11 graphically shows fluorophotometric units correlated with questionnaire scores for fluorescein clearance and corrected fluorescein clearance test scores.
Figure 12:
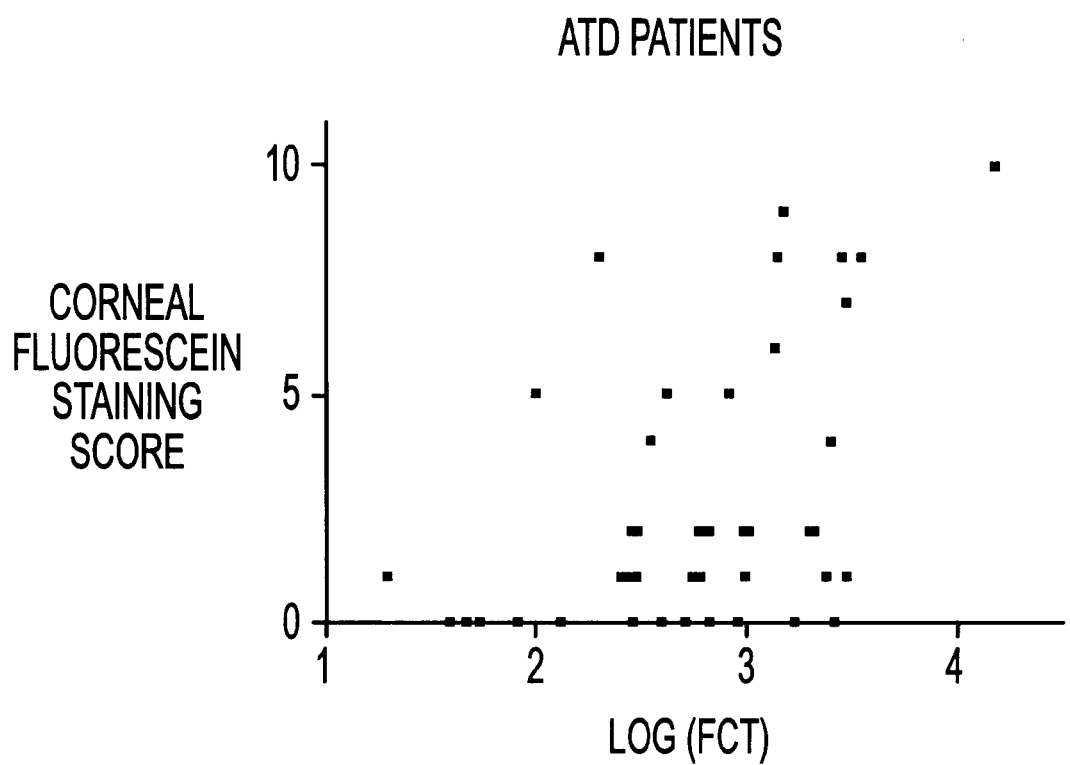
FIG. 12 graphically shows corneal fluorescein staining scores plotted against the logarithm of fluorescein clearance test scores for aqueous tear deficiency patients.
Figure 13:
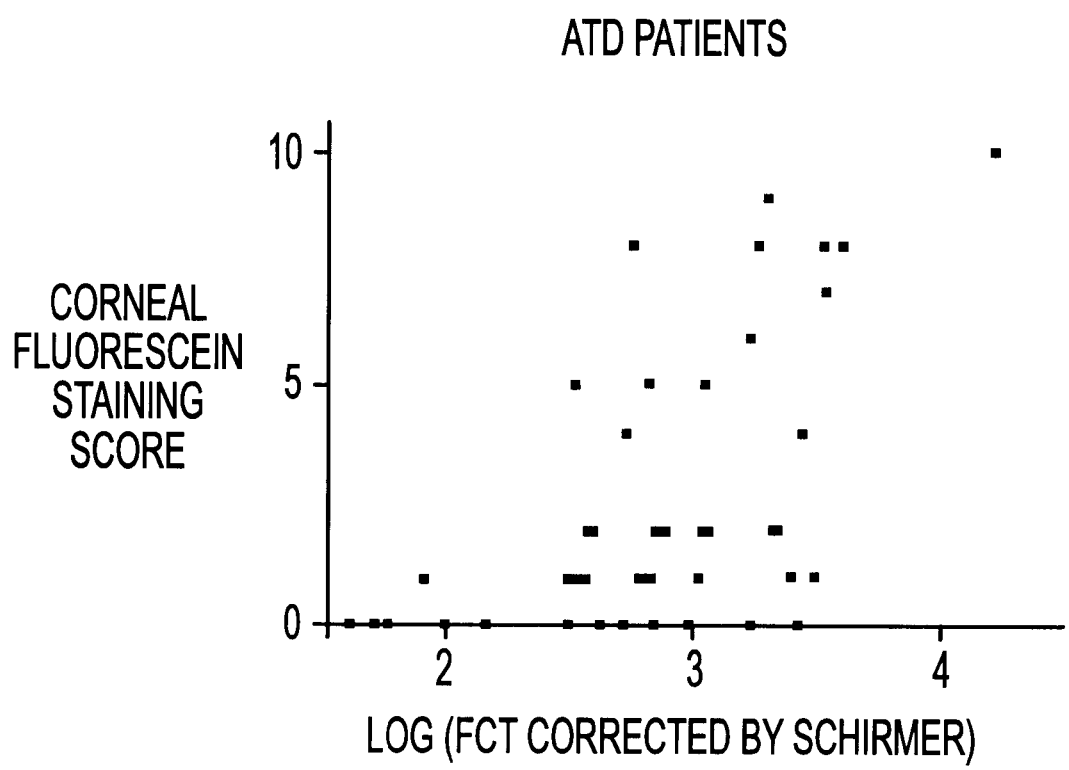
FIG. 13 graphically shows corneal fluorescein staining scores plotted against the logarithm of fluorescein clearance test scores corrected by Schirmer 1 figures for aqueous tear deficiency patients.
Figure 14:
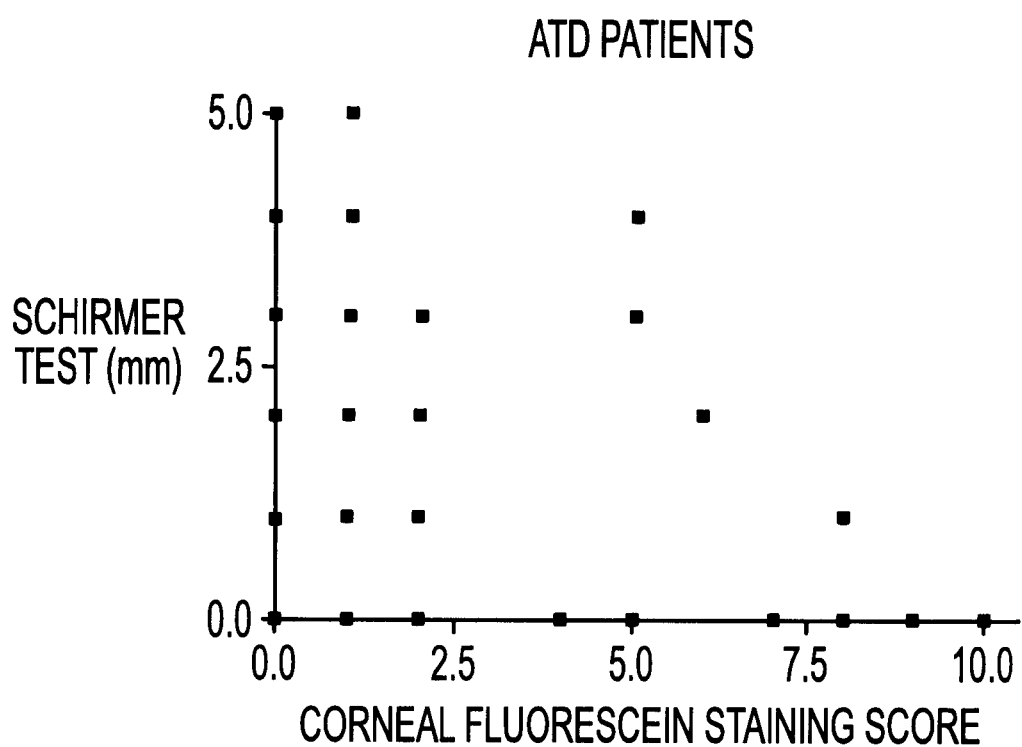
FIG. 14 graphically shows Schirmer 1 test scores plotted against corneal fluorescein staining scores for aqueous tear deficiency patients.
Figure 15:
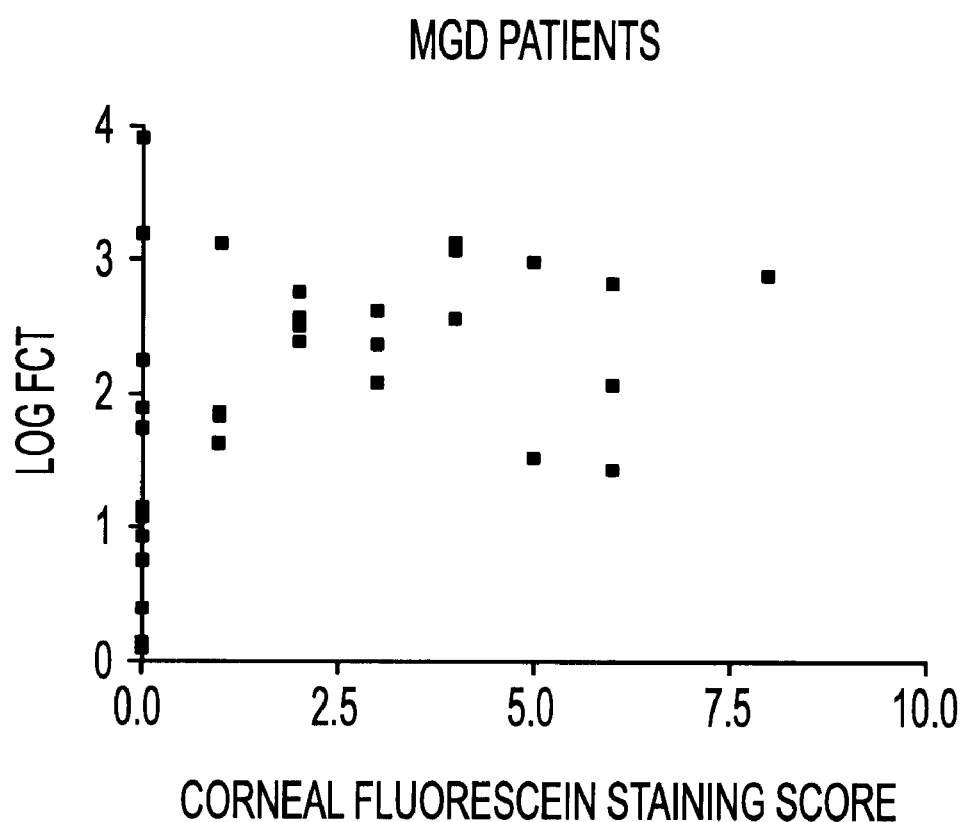
FIG. 15 graphically shows logarithm of fluorescein clearance test scores plotted against corneal fluorescein staining scores for meibomian gland disease patients.
Figure 16:
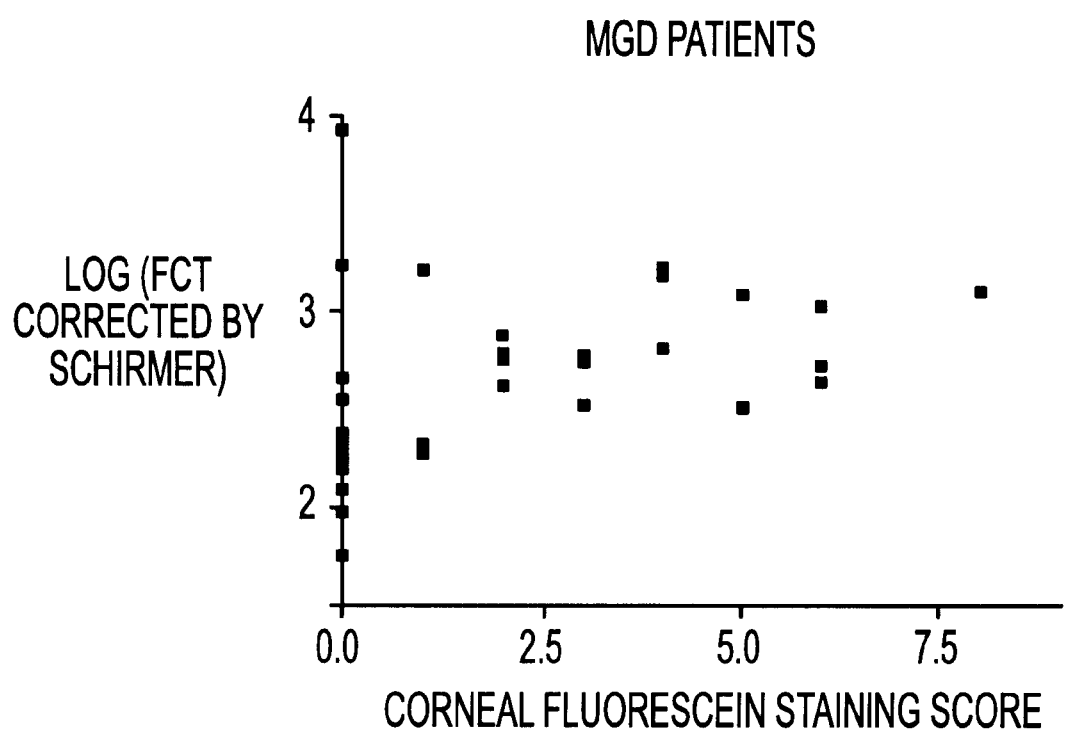
FIG. 16 graphically shows logarithm of fluorescein clearance test scores corrected by Schirmer 1 test figures plotted against corneal fluorescein staining scores for meibomian gland disease patients.
Figure 17:
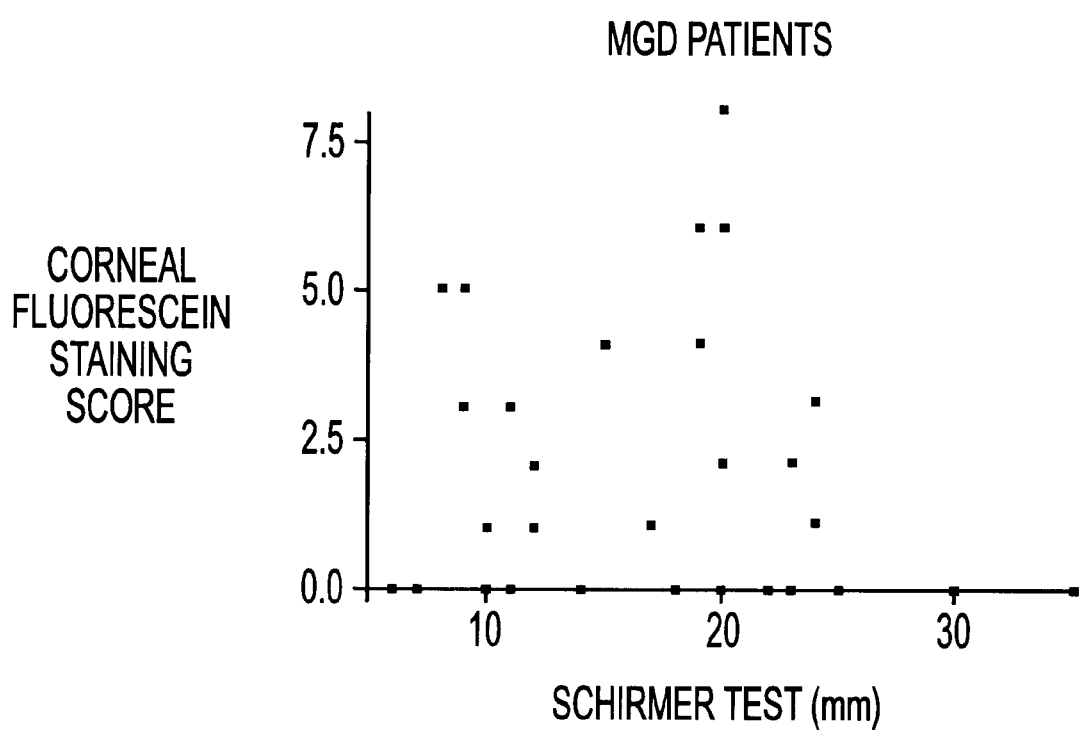
FIG. 17 graphically shows corneal fluorescein staining scores plotted against Schirmer 1 test scores for meibomian gland disease patients.
Figure 18:
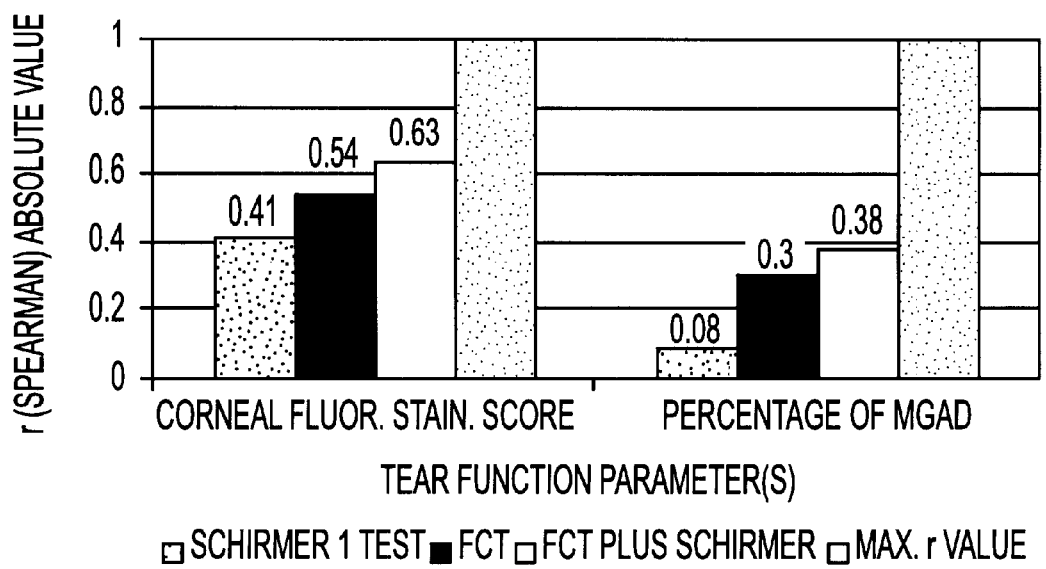
FIG. 18 graphically shows Spearman rank correlation plotted against tear function parameters for the following groups: Schirmer test scores; Fluorescein Clearance Test (FCT), Fluorescein Clearance Test (FCT) corrected by Schirmer values; and maximal Spearman rank correlation values.

Correlations between the symptom questionnaire score, the Schirmer 1 test score, the corneal fluorescein staining score, the FCT and the corrected FCT are provided in Table 6 and in FIGS. 10 and 11.

The results of correlation analyses between the Schirmer test, the FCT, the corrected FCT, eyelid and meibomian gland pathology (anterior migration of Marx's line, meiboand patients with tear film disorders due to meibomian gland disease (MGD) and/or aqueous tear deficiency (ATD). These studies were performed to gain a greater understanding regarding the factors that cause ocular surface disease. The results of these studies may improve the ability of clinicians to identify a tear film disorder as the cause of a patient's ocular surface disease.

TABLE 6

Correlation between Questionnaire score, Fluorescein Clearance Test (FCT), corrected FCT, Schirmer Test and corneal fluorescein staining scores.

| Healthy subjects | FCT (fluorophotometric units/µl) | Corrected FCT | Corneal Fluorescein Staining | Schirmer Test (mm.) |
|---|---|---|---|---|
| Questionnaire score MGD patients | $r_p = 0.07$ P = n.s. | $r_p = 0.02$ P = n.s. | — | $r_p = -0.14$ P = n.s. |
| Questionnaire score ATD patients | $r_p = 0.35$ P = 0.039 | $r_p = 0.36$ P = 0.032 | $r_p = -0.33$ P = 0.049 | $r_p = -0.36$ P = 0.028 |
| Questionnaire score All patients | $r_s = 0.53$ P = 0.0002 | $r_s = 0.54$ P < 0.0001 | $r_s = 0.63$ P < 0.0001 | $r_p = -0.15$ P = n.s. |
| Questionnaire score | $r_s = 0.35$ P = 0.0004 | $r_s = 0.37$ P < 0.0001 | $r_s = 0.47$ P < 0.0001 | $r_s = -0.34$ P = 0.0006 |

Correlation coefficients ($r_p$ = Pearson correlation coefficient; $r_s$ = Spearman correlation coefficient)
n.s. = not significant.
MGD = meibomian gland disease
ATD = aqueous tear deficiency

TABLE 7

Correlation coefficients and statistical significance (P) between Fluorescein Clearance Test (FCT), corrected FCT, Schirmer Test, corneal fluorescein staining score, anterior migration of Marx's line, percentage of Meibomian gland acinar dropout (MGAD), orifice metaplasia score, cornea and conjunctiva sensitivity score.

| All subjects | FCT (fluorophotometric units/$\mu$l) | Corrected FCT | Schirmer Test (mm.) |
|---|---|---|---|
| Schirmer Test (mm.) | $r_s = -0.57$ P < 0.0001 | — | — |
| Corneal Fluorescein Staining score | $r_s = 0.54$ P < 0.0001 | See Table 4 | $r_s = -0.41$ P < 0.0001 |
| Anterior migration of Marx's line | $r_s = 0.23$ P = 0.025 | $r_s = 0.28$ P = 0.0037 | $r_s = 0.01$ P n.s. |
| Percentage of MGAD | $r_s = -0.30$ P = 0.002 | $r_s = -0.38$ P = 0.0001 | $r_s = -0.08$ P n.s. |
| Orifice metaplasia score | $r_s = 0.34$ P = 0.0006 | $r_s = 0.37$ P < 0.0001 | $r_s = -0.04$ P n.s. |
| Cornea sensitivity | $r_s = -0.34$ P = 0.0009 | $r_s = -0.35$ P = 0.0003 | $r_s = 0.35$ P = 0.0004 |
| Conjunctiva sensitivity | $r_s = -0.34$ P = 0.0007 | $r_s = -0.35$ P = 0.0002 | $r_s = 0.36$ P = 0.0003 |

Correlation coefficients ($r_p$ = Pearson correlation coefficient; $r_s$ = Spearman correlation coefficient)
n.s. = not significant

TABLE 8

Correlations between Fluorescein Staining score and Schirmer test, FCT and FCT corrected with the formula based only on Schirmer test (FCT (corrected) = FCT + Schirmer score · 4) for Meibomian Gland Disease (MGD) patients and Aqueous Tear Deficiency (ATD) patients.

| Fluorescein staining score | Schirmer test (mm.) | FCT (fluorophotometric units/$\mu$l) | FCT Schirmer corrected |
|---|---|---|---|
| MGD patients | $r_s = -0.06$ P n.s. | $r_s = 0.47$ P = 0.0033 | $r_s = 0.58$ P = 0.0002 |
| ATD patients | $r_s = -0.38$ P = 0.011 | $r_s = 0.43$ P = 0.0036 | $r_s = 0.54$ P = 0.0002 |
| All subjects | $r_s = -0.41$ P < 0.0001 | $r_s = 0.54$ P < 0.0001 | $r_s = 0.63$ P < 0.0001 |

$r_s$ = Spearman rank correlation coefficient.
n.s. = not significant

Previously, it was found that the FCT showed greater correlation with irritation symptoms than the Schirmer 1 test, whereas, the Schirmer 1 test showed slightly better correlation with the severity of corneal fluorescein staining. In this embodiment, a different patient population was studied, wherein the FCT showed better correlation with both irritation symptoms and corneal fluorescein staining scores than the Schirmer 1 test. These findings indicate that clearance of tears from the ocular surface is a key factor in the pathogenesis of keratoconjunctivitis sicca. These correlations were further improved by adding a correction factor for the Schirmer test result to the FCT score.

This indicates that the correlation of decreased aqueous tear production with ocular irritation and ocular surface disease is not solely due to an effect on reducing tear clearance. Indeed, secretory dysfunction of the lacrimal gland may promote ocular surface inflammation and decrease delivery of protective proteins and growth factors needed to maintain ocular surface homeostasis. Patients with Sjogren's syndrome exhibit a pattern wherein as aqueous tear production decreases, levels of inflammatory cytokines in the conjunctival epithelium and tear fluid increase, while the concentration of epidermal growth factor (EGF) in the tear fluid decreases.

The corrected FCT is a relatively easy test for clinicians to perform. Unlike tear osmolarity, a diagnostic technique for diagnosis of dry eye that requires expensive instrumentation, tear fluorescein clearance can be assessed in an inexpensive fashion by practitioners. The use of colorimetric techniques to evaluate tear clearance by collecting fluorescein stained tear fluid on a Schirmer test strip is well known in the ophthalmic art. However, in another embodiment of the invention discussed in Example IV, a seven-point visual scale is described which correlates tear fluorescein clearance with the results of the fluorometric technique used in the invention.

Skilled artisans recognize that anesthesia of the ocular surface decreases aqueous tear production. The results of this study support recently proposed unified concepts for development of dry eye wherein perturbations on the ocular surface negatively affect tear fluid secretion by the lacrimal glands by inhibiting afferent sensory responses to efferent cholinergic neural reflex loops. Both decreased aqueous tear production and delayed tear clearance are associated with decreased ocular surface sensation. Decreased ocular surface sensation could explain why patients with MGD were noted to have significantly reduced aqueous tear production compared to a control group of similar age and gender (Table 5). Patients with MGD and lipid tear deficiency have been noted to have increased tear film evaporation and a decreased tear volume. These factors alone could be responsible for the delayed tear clearance and the secondary changes to the eyelid and ocular surface that occur in meibomian gland disease. Regardless of the mechanism by which tear clearance decreases in MGD, delayed tear clearance leads to decreased ocular surface sensation and decreased sensory stimulation of lacrimal gland tear secretion. This creates a viscious, self-perpetuating cycle on the ocular surface.

An intriguing finding of this study was that the FCT, and to a greater degree the FCT corrected by the Schirmer test, showed very strong correlation with the pathologic changes of the eyelid margin that develop in patients with MGD, as shown in Table 7. It is possible that the biochemical changes in the tear fluid that accompany delayed tear clearance, such as an increased concentration of the inflammatory cytokine interleukin 1 (IL-1) and increased activity of the matrix degrading enzyme, matrix metalloproteinase 9 (MMP-9) could be responsible for these changes. These changes could also explain the increased prevalence of MGD in patients with severe ATD, a condition where tear clearance is markedly decreased. Future research may identify the mechanism (s) by which delayed tear clearance decreases ocular surface sensation and promotes corneal epithelial and eyelid disease. The results described herein indicate that the corrected FCT appears to be even a better tool to study these mechanisms than the FCT alone.

Example IV

In a preferred embodiment of the invention, the correlation and agreement between the inventive validated fluorometric technique is established with a novel, clinically practical, standardized visual scale for assessing tear fluorescein clearance.

Research was conducted by medically qualified personnel in strict accordance with the guidelines of the University of Miami School of Medicine Institutional Review Board and in accordance with the Tenets of the Declaration of Helsinki.

Dry eye patients had no history of ocular surgery, contact lens use, punctal occlusion or of eye drops use (other than non-preserved artificial tears). Adult patients presenting with complaints of ocular irritation were evaluated by the investigators at the Ocular Surface Center (Bascom Palmer Eye Institute—University of Miami School of Medicine) and at the Department of Neurological and Visual Sciences (Di.N.V.S., Opthalmology R, University of Genova—Italy). Each subject was first asked to complete a symptom questionnaire consisting of 11 questions describing the severity and the nature of their irritation symptoms (Table 1). The patients then underwent a panel of diagnostic tests that were performed in the following order: corneal and conjunctival sensitivity, fluorescein clearance test, standardized visual scale test, evaluation of corneal fluorescein staining, Schirmer 1 test and slit lamp biomicroscopic exam evaluating the lid margins and meibomian glands. Based on the results of these tests, patients were classified into one of three groups based on the following inclusion criteria.

Patients exhibiting aqueous tear deficiency had a Schirmer 1 test$\leq$5 in at least one eye and a questionnaire score>5.

Patients exhibiting meibomian gland disease had a Schirmer 1 test>5 in both eyes and a questionnaire score>5. These patients were classified as having rosacea associated (inflammatory) MGD or non-inflammatory meibomian gland atrophy.

Diagnosis of rosacea was based on previously reported criteria and required the presence of at least two facial signs of rosacea (which include rhinophyma, telengiectasia, persistent erythema, papules, pustules, and hypertrophic sebaceous glands in facial flush areas) and hyperemia of lid margins (brush marks) and/or conjunctival hyperemia. Atrophic MGD was defined as at least 30% atrophy of meibomian gland acini in lower lid (determined by transillumination of lower lid as described below), no facial signs of rosacea, and mild or no hyperemia of the lid margins or conjunctiva.

A group of 32 normal subjects of similar age and gender distribution was evaluated as a control group. Subjects were considered normal if they had no history of ocular irritation (symptom score<5), use of eyedrops, and had a Schirmer 1 test score>10 mm.

The Fluorescein-Clearance Test was performed as described hereinabove. Briefly, 5 $\mu l$ of 2% Fluorescein (IOLAB, Claremont, Calif.) were instilled into the inferior conjunctival cul-de-sac. After 15 min, fluorescein-stained tear fluid was collected atraumatically with a porous polyester rod from the inferior lateral tear meniscus under direct slit-lamp observation, minimizing irritation of the ocular surface or lid margin. Immediately after tear collection, the tubes were placed in sealed polypropylene tubes and were protected from light until fluorophotometric analysis. The volume of the collected tear fluid was determined by the weight difference between the rod containing the sample and the precollection empty rod using an OHAUS Model GA110 scale (OHAUS, Bern, Switzerland). Rods were then placed into the end of a micropipette tip located within a 0.5-ml Eppendorf tube and a volume of phosphate-buffered saline (100 $\mu l$—weight of rod in micrograms) was added to the end of the rod. The tubes were then spun at 12,000 revolutions per minute for 5 minutes, and the fluid was transferred to wells of a 96-well polycarbonate microtiter plate (Corning 96, Corning, N.Y.). Fluorescence was measured within 24 hours after collection of the tear fluid using a fluorescence multiplate reader (Cytofluor II fluorometer—PerSeptive Biosystems, MA). Corrected FCT was calculated by using the formula:

$$FCT(\text{corrected})=FCT+\text{Schirmer score}. \quad (4)$$

Figure 19:
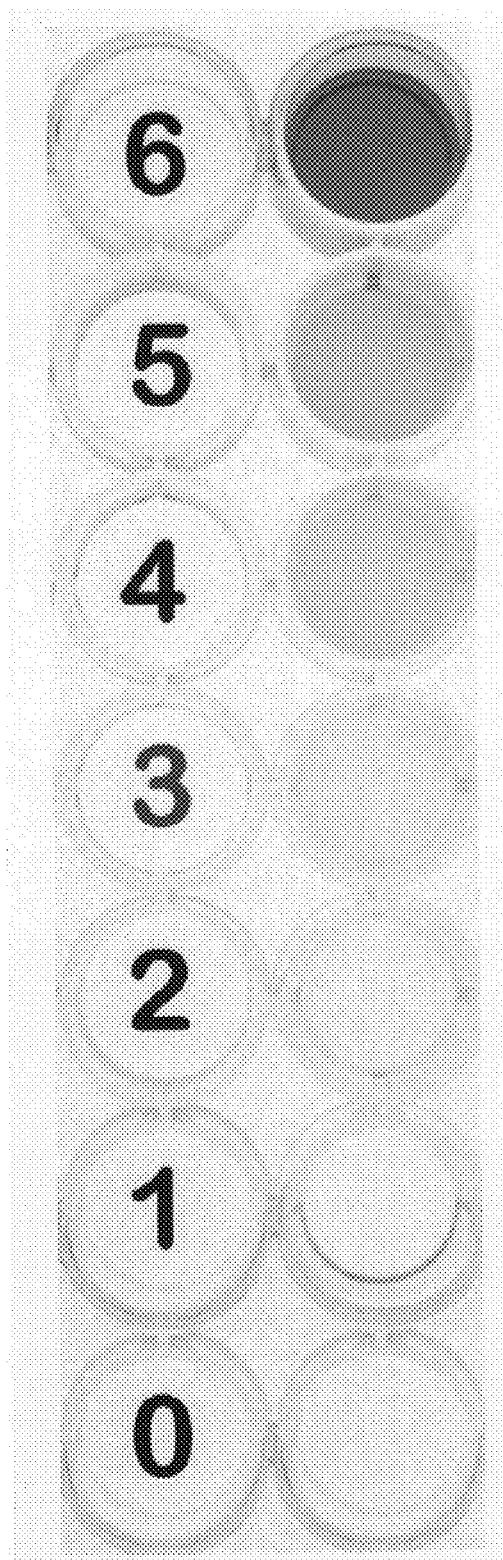
FIG. 19 shows a standardized scale to visually evaluate Fluorescein Clearance. Numbers on the left correspond to dilutions of fluorescein and fluorometric values provided in Table 9. A score of 3 indicates the cut-off value between normality and abnormality.

The standardized visual scale had a score ranging from 0 to 6. (FIG. 19 and Table 9). A score of 3 corresponded to a fluorophotometric value of 274 fluorescein units/$\mu l$, the previously reported threshold between normality and abnormality (See Afonso et al. supra). The threshold value between symptomatic and asymptomatic patients is a fluorescein clearance fluorophotometric value of 274 units/microliter. This corresponds to a score of 3 on the visual scale. The fluorophotometric values corresponding to the scores of 1 and 2 were arbitrarily chosen. The fluorophotometric values corresponding to the score of 5 was chosen by taking into consideration that the majority of patients with delayed tear fluorescein clearance are known to have fluorometric scores in the range of 274–3248 units/microliter (corresponding to a visual score between 3 and 5). Then a score of 4 (812 units/microliter) was added to separate patients with a mild delayed tear fluorescein clearance from those with a severe delayed tear fluorescein clearance. Only a minority of patients with aqueous tear deficiency and/or severe meibomian gland disease were found to have fluorescein concentration greater than 3248 units/microliter (that corresponds to a visual score between 5 and 6).

TABLE 9

Standardized visual scale.

| SCORE | DILUTION (2% Fluorescein:PBS) | Fluorophotometric value (units/$\mu l$) |
|---|---|---|
| 0 | PBS | 1 |
| 1 | 1:8000 | 50.5 |
| 2 | 1:4000 | 101.5 |
| 3 | 1:1482 | 274 |
| 4 | 1:500 | 812 |
| 5 | 1:125 | 3248 |
| 6 | Undiluted 2% Fluorescein | oversaturated |

PBS = phosphate buffered saline

Figure 20:
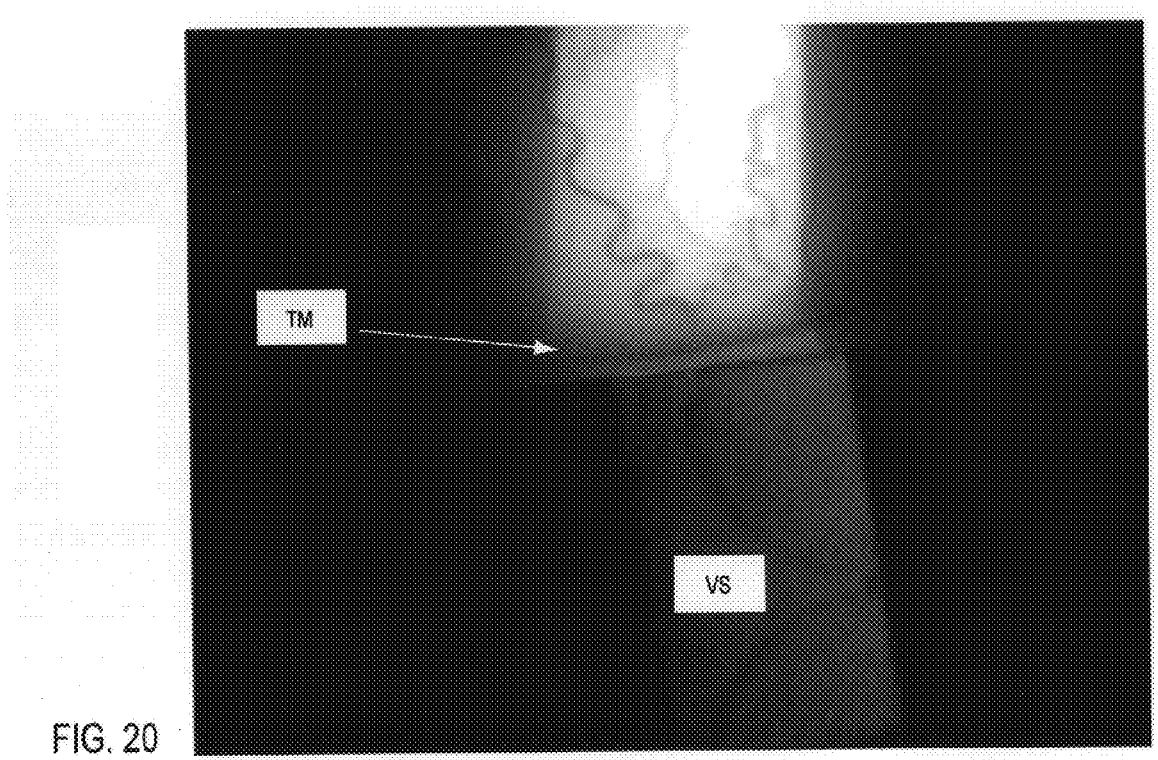
FIG. 20 shows the results of a standardized visual scale (score=0) for a healthy subject. The arrowhead indicates tear meniscus (TM) on lateral portion of lower lid. VS represents visual color scale.
Figure 21:
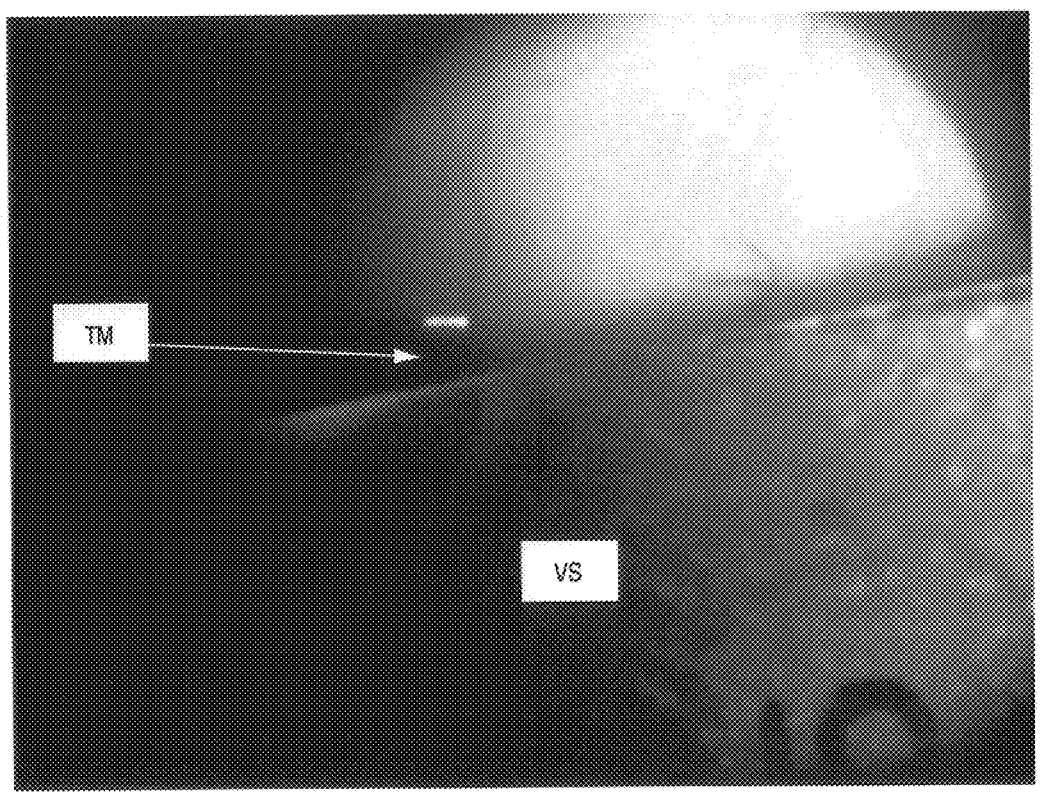
FIG. 21 shows the results of a standardized visual scale for a patient with meibomian gland disease (MGD) and delayed tear clearance. The standardized visual score equals 5 in this patient. The arrowhead indicates tear meniscus (TM) on lateral portion of lower lid. VS represents visual color scale.

Immediately before the tear collection for fluorometric analysis, the color of the tear meniscus in the third lateral of the lower lid was visually compared with one of the colors of the standardized visual scale (FIGS. 20 and 21). If the color of a tear meniscus was judged to be in-between two of the six standard scale colors, that score was graded between these two standard colors. For example, if the color was stronger than 2 but weaker than 3, it would be graded 2.5.

For calculation of sensitivity, specificity and diagnostic precision, the number 0 was assigned to subjects whose visual scale score was lower than 3 (normality), the number 1 was assigned if the score was higher than 3 (disease) and the score 2 was given if it was not clear if the color was higher or lower than 3 (equivocal).

A patient's ocular surface was examined with a biomicroscope and the x10 objective under blue-light illumination two minutes after fluorescein instillation into the tear film. The intensity of corneal fluorescein staining was recorded as previously described in each of four quadrants on the cornea: temporal, nasal, superior and inferior using a standardized 4 point scale (0=none; 1=mild; 2=moderate; 3=severe). The range of staining scores was from 0 to 12.

Without previously instilling anesthetic drops, Schirmer paper test strips (Alcon Laboratories, Fort Worth, Tex.) were placed over the lid margin at the junction of the lateral and middle thirds of the lower eyelid for 5 min. The millimeters of strip wetting were measured and recorded.

Cornea and conjunctiva sensitivity were assessed with the Cochet-Bonnet esthesiometer (Luneau Ophtalmologie, Chartres Cedex, France). The stimulus from the Cochet Bonnet consists of a nylon filament that can be varied in length from 0 to 6 cm. The procedure for measuring ocular surface sensitivity was as follows: under visual control, the nylon filament of the Cochet Bonnet instrument was approached smoothly and perpendicularly toward the center of the cornea. Contact was detected by the slightest bend of the nylon; sensitivity was taken as the length of the filament that gave a 50% positive response from a minimum of four stimulus applications. Subject reliability was tested by bringing the filament close to the cornea without actually touching. The same procedure was used to test conjunctiva sensation with the stimulus applied to the middle of the exposed temporal-bulbar conjunctiva.

The meibomian gland orifices of test subjects were examined by slit-lamp biomicroscopy for the presence of metaplasia (abnormal growth and keratinization of duct epithelium manifesting as white shaft protruding from the orifices). The inferior tarsus was transilluminated with a halogen Finhoff transilluminator (Welch Allyn, Schenectady, N.Y.) and the percentage of meibomian gland acinar dropout was quantitated as previously reported.

The presence of irregularity of the lid margin and of anterior migration of Marx line was evaluated by slit-lamp biomicroscopy. Anterior migration of Marx line was determined using criteria as discussed hereinabove (See Norn supra).

For statistical evaluations only the right eye was considered for each patient. Data distribution was analyzed. If data were normally distributed, parametric statistical tests were used; otherwise non-parametric tests were utilized. The differences in age among the three groups (normal controls, patients with meibomian gland disease and patients with aqueous tear deficiency) were studied by means of one-way analysis of variance and Bartlett's test for equal variances. The difference in gender among the three groups was studied using the Kruskal Wallis Statistic.

In order to allow statistical analysis, every SVST score of 2 was changed to either 1 or 0 according to a series of random numbers generated by Excel 5.0 (Microsoft).

Furthermore, in order to study the correlations between SVST and the other parameters, the score ranging from 0 to 6 (in 0.5 unit increments) was used.

In order to improve or increase the sensitivity of the SVST, correction formula II was used:

$$\text{SVST (corrected)} = \text{SVST} + \frac{\text{Schirmer score}}{y} \quad \text{II}$$

The coefficient y was calculated by looking for the best area under the Receiver Operating Characteristic (ROC) curves as described hereinabove.

Correlation coefficients were calculated between the FCT, corrected FCT, SVST, corrected SVST and questionnaire score, Schirmer 1 test, corneal fluorescein staining score, anterior migration of Marx line, percentage of Meibomian gland acinar loss, presence of orifice metaplasia (0=absent, 1=present) and cornea and conjunctiva sensitivity scores. If data distribution was normal, then the Pearson correlation coefficient was used; otherwise the Spearman rank correlation coefficient was calculated.

Sensitivity, specificity and diagnostic precision of FCT, corrected FCT, SVST and corrected SVST in diagnosing ATD and MGD were calculated.

K statistic was used to evaluate the agreement among SVST, corrected SVST, FCT, corrected FCT. All statistical calculations were performed by means of GraphPad Prism 2.0 Software and Excel 5.0 (Microsoft).

No significant differences in age and gender were found between normal control subjects (n=32, average age=59.79 standard deviation=14.60), patients with MGD (n=54, average age=60.15 standard deviation=13.95) and patients with ATD (n=39, average age 60.38=standard deviation=14.23); for age, a one-way analysis of variance was used (P=0.371), the Bartlett's statistic (corrected) (P=0.483); for gender, the Kruskal Wallis Statistic was used (P=0.341). Thirty of the MGD patients had rosacea and twenty-four had non-inflammatory atrophic disease. The two groups of MGD patients were combined for statistical analysis because there was no statistically significant differences between the two groups for Schirmer 1 test, FCT, SVST and corneal and conjunctival sensitivity.

The mean and the standard deviation values of diagnostic tests, as well as the statistically significant differences among the 3 studied groups are provided in Table 10. The best value for the coefficient y in the correction formula for SVST was calculated to be 35. Thus, the best correction formula is:

$$\text{SVST corrected} = \text{SVST score} + \frac{\text{Schirmer score}}{35}$$

The sensitivity of the FCT in diagnosing MGD was 67%, and in diagnosing ATD it was 95%. The specificity was 97%. The diagnostic precision of the FCT was 78% for MGD and 94% for ATD. By applying the correction factor, the sensitivity of the FCT in diagnosing MGD was raised to 72% and in diagnosing ATD to 97%. The diagnostic precision of the FCT corrected was raised to 80% for MGD and to 96% for ATD. The differences in FCT corrected among the three groups was found to be statistically significant (Kruskal Wallis statistic=45.07 P<0.0001), and also the differences in FCT corrected between MGD and ATD patients were statistically significant (Mann Whitney U =436.0 P=0.0102) (Table 3).

TABLE 10

Statistical comparison of three groups [Normal control subjects, Meibomian Gland Disease (MGD) and Aqueous Tear Deficiency (ATD) patients].

| Group | Corneal fluorescein Staining score | Schirmer 1 test | % Meibomian Gland Atrophy | Meibomian Gland Orifice Metaplasia | FCT |
|---|---|---|---|---|---|
| Normal controls (n = 32) | 0.0 ± 0.0 | 22.6 ± 7.7 | 4.8 ± 8.2 | 0.1 ± 0.3 | 90.7 ± 63.3 |
| MGD (n = 54) | 0.6 ± 0.9 | 16.6 ± 8.1 | 57.3 ± 31.1 | 0.9 ± 0.3 | 1740 ± 2294 |
| Differences Between Normals and MGD | — | t = 3.515 P = 0.0007 | U = 122.5 P < 0.0001 | U = 198.0 P < 0.0001 | U = 298.5 P < 0.0001 |
| ATD (n = 39) | 2.5 ± 3.0 | 2.7 ± 1.7 | 24.5 ± 34.7 | 0.6 ± 0.3 | 3707 ± 4824 |
| Differences Between MGD and ATD | U = 796.5 P = 0.0450 | t = 11.01 P < 0.0001 | U = 475.0 P = 0.0012 | U = 751.0 P = 0.0186 | U = 729.0 P = 0.0118 |
| Differences Among the 3 groups | K = 31.29 P < 0.0001 | F = 92.39 P < 0.0001 | K = 50.77 P < 0.0001 | K = 54.03 P < 0.0001 | K = 48.30 P < 0.0001 |

| Group | Corrected FCT | SVST | Corrected SVST | Corneal Sensation | Conj. Sensation |
|---|---|---|---|---|---|
| Normal controls (n = 32) | 182.6 ± 69.4 | 1.1 ± 0.8 | 1.7 ± 0.8 | 5.4 ± 0.8 | 1.4 ± 0.5 |
| MGD (n = 54) | 1834 ± 2292 | 3.2 ± 1.2 | 3.7 ± 1.1 | 4.3 ± 1.2 | 0.8 ± 0.7 |
| Differences Between Normals and MGD | U = 302.5 P < 0.0001 | U = 265.5 P < 0.0001 | U = 198.0 P < 0.0001 | U = 137.0 P < 0.0001 | U = 126.0 P < 0.0001 |
| ATD (n = 39) | 3822 ± 4822 | 4.0 ± 0.9 | 4.1 ± 0.9 | 2.9 ± 1.6 | 0.6 ± 0.3 |
| Differences Between MGD and ATD | U = 731.0 P = 0.0123 | U = 844.5 P = 0.1067 n.s. | U = 904.5 P = 0.2514 n.s. | U = 495.1 P = 0.0018 | U = 939.2 P = 0.3295 n.s. |
| Differences Among the 3 groups | K = 48.00 P < 0.0001 | K = 65.81 P < 0.0001 | K = 76.82 P < 0.0001 | K = 22.37 P < 0.0001 | K = 24.40 P < 0.0001 |

Average ± standard deviation.
U = Mann Whitney U test.
t = two tailed unpaired t test.
K = Kruskal Wallis statistic.
F = One-way analysis of variance
FCT = fluorescein clearance test
Corrected FCT = FCT corrected by Schirmer test score and corneal fluorescein staining score
SVST = standardized visual scale test
Corrected SVST = SVST corrected by Schirmer test score
n.s. = not significant The sensitivity of the SVST in diagnosing MGD was 69%, and in diagnosing ATD it was 97%. The specificity was 97%. The diagnostic precision of the SVST was 79% for MGD and 97% for ATD. By applying the correction factor, the sensitivity of the SVST in diagnosing MGD was raised to 76% and in diagnosing ATD it remained the same (at 97%); however, the specificity was decreased to 94%. The diagnostic precision of the SVST corrected was raised to 83% for MGD and decreased to 96% for ATD. The differences in SVST and SVST corrected among the three groups was found to be statistically significant (respectively Kruskal Wallis statistic=54.18 and 44.64 P<0.0001), and also the differences in SVST between MGD and ATD patients were statistically significant (Mann Whitney U=368.0 P=0.0009) (Table 10).

Correlations between symptom questionnaire score, Schirmer test scores, corneal fluorescein staining score, FCT and corrected FCT are provided in Table 11.

The results of correlation analyses between Schirmer test, FCT, corrected FCT, eyelid and meibomian gland pathology (anterior migration of Marx line, meibomian gland orifice metaplasia, percentage of meibomian gland acinar dropout) and cornea and conjunctiva sensitivity scores are presented in Table 12.

The k statistic, used to study the agreement among FCT, SVST, corrected FCT and corrected SVST, resulted to be 0.925 (95% confidence interval=0.895–0.955).

TABLE 11

Correlation between Questionnaire score and Fluorescein Clearance Test (FCT), Standardized Visual Scale test (SVST), SVST corrected by Schirmer test score, Schirmer Test and corneal fluorescein staining scores.

| All patients | FCT | Corrected FCT | SVST | Corrected SVST | Corneal Fluorescein Staining score | Schirmer test score |
|---|---|---|---|---|---|---|
| Questionnaire score | $r_s = 0.462$ $P < 0.0001$ | $r_s = 0.457$ $P < 0.0001$ | $r_s = 0.670$ $P < 0.0001$ | $r_s = 0.618$ $P < 0.0001$ | $r_s = 0.504$ $P < 0.0001$ | $r_p = -0.437$ $P < 0.0001$ |

Correlation coefficients ($r_p$ = Pearson correlation coefficient; $r_s$ = Spearman correlation coefficient)
FCT = fluorescein clearance test
Corrected FCT = FCT corrected by Schirmer test score and corneal fluorescein staining score
SVST = standardized visual scale test
Corrected SVST = SVST corrected by Schirmer test score

TABLE 12

Correlation coefficients and statistical significance (P) between Fluorescein Clearance Test (FCT) and Schirmer Test, corneal fluorescein staining score, anterior migration of Marx's line, percentage of Meibomian gland acinar dropout (MGAD), orifice metaplasia score, cornea and conjunctiva sensitivity score.

| All subjects | FCT | Corrected FCT | SVST | Corrected SVST | Schirmer Test |
|---|---|---|---|---|---|
| SVST | $r_s = 0.862$ $P < 0.0001$ | $r_s = 0.722$ $P < 0.0001$ | — | $r_s = 0.966$ $P < 0.0001$ | $r_p = -0.460$ $P < 0.0001$ |
| Corrected SVST | $r_s = 0.845$ $P < 0.0001$ | $r_s = 0.726$ $P < 0.0001$ | $r_s = 0.966$ $P < 0.0001$ | — | $r_p = -0.326$ $P = 0.0002$ |
| Schirmer Test | $r_p = -0.325$ $P = 0.0002$ | $r_p = -0.270$ $P = 0.0023$ | $r_p = -0.460$ $P < 0.0001$ | $r_p = -0.326$ $P = 0.0002$ | — |
| Corneal Fluorescein Staining score | $r_s = 0.447$ $P < 0.0001$ | $r_s = 0.416$ $P < 0.0001$ | $r_s = 0.603$ $P < 0.0001$ | $r_s = 0.543$ $P < 0.0001$ | $r_s = -0.375$ $P < 0.0001$ |
| Anterior migration of Marx's line | $r_s = 0.291$ $P = 0.001$ | $r_s = 0.337$ $P = 0.0005$ | $r_s = 0.377$ $P < 0.0001$ | $r_s = 0.370$ $P < 0.0001$ | $r_s = -0.182$ $P = 0.04$ |
| Percentage of MGAD | $r_s = 0.343$ $P < 0.0001$ | $r_s = 0.440$ $P < 0.0001$ | $r_s = 0.579$ $P < 0.0001$ | $r_s = 0.556$ $P < 0.0001$ | $r_s = -0.311$ $P < 0.0001$ |
| Orifice metaplasia score | $r_s = 0.417$ $P < 0.0001$ | $r_s = 0.486$ $P < 0.0001$ | $r_s = 0.574$ $P < 0.0001$ | $r_s = 0.588$ $P < 0.0001$ | $r_s = -0.305$ $P < 0.0001$ |
| Cornea sensitivity | $r_s = -0.495$ $P < 0.0001$ | $r_s = -0.497$ $P < 0.0001$ | $r_s = -0.589$ $P < 0.0001$ | $r_s = -0.504$ $P < 0.0001$ | $r_s = 0.506$ $P < 0.0001$ |
| Conjunctiva sensitivity | $r_s = -0.218$ $P = 0.0377$ | $r_s = -0.211$ $P = 0.0356$ | $r_s = -0.347$ $P < 0.0001$ | $r_s = -0.254$ $P < 0.0001$ | $r_s = 0.305$ $P < 0.0001$ |

Correlation coefficients ($r_p$ = Pearson correlation coefficient; $r_s$ = Spearman correlation coefficient)
FCT = fluorescein clearance test
Corrected FCT = FCT corrected by Schirmer test score and corneal fluorescein staining score
SVST = standardized visual scale test
Corrected SVST = SVST corrected by Schirmer test score Delayed clearance of fluorescein dye instilled on to the ocular surface showed greater correlation with ocular irritation symptoms, corneal and conjunctival sensitivity and corneal fluorescein staining than the Schirmer 1 test. Assessment of tear fluorescein concentration in these studies was performed with a sophisticated and expensive commercial fluorometer.[1] While this technique was adequate for research studies to establish the value of assessing tear fluorescein clearance as a risk factor for ocular irritation and ocular surface disease, it is not practical for routine clinical use. Techniques for routine clinical evaluation of tear fluorescein clearance, including the use of Schirmer test strips to collect fluorescein-stained tears, have been evaluated. The inventors noted several problems with the Schirmer test strip technique that can induce inaccuracies in assessment of tear fluorescein concentration. First, it is difficult to compare color on the strip with the Schirmer test photographic standards of liquid fluorescein of different concentration. Second, the intensity of the fluorescein color on the strip is affected by the length of strip wetting. For example, a tear fluorescein concentration of 250 units appears different on a strip wet 4 mm than on a strip wet 30 mm. Thus, the invention provides an easier and more accurate method of assessment, comprising directly comparing the color of the fluorescein-stained lateral tear meniscus with a photographic standard of liquid fluorescein.

The current study validated this standard visual scale by comparing its results with the previously reported fluorometric technique in normal subjects and those with MGD and/or ATD. The visual scale was found to have equivalent sensitivity and specificity to the more sophisticated fluorometric technique for identifying delayed tear clearance. The visual scale also showed similar correlation with irritation symptoms and eyelid and corneal epithelial disease as the fluorometric technique and it was further improved by applying a correction factor based on the Schirmer test scores.

The newly developed standardized visual scale for assessing tear fluorescein clearance is an easy and inexpensive method for routine clinical assessment of tear fluorescein clearance. This technique should facilitate more widespread use of tear fluorescein clearance for diagnosis and may identify patients that will benefit from pharmacological therapy of the ocular surface inflammation that accompanies delayed tear clearance.

References

1. Pflugfelder S C, Tseng S C G, Sanabria O, et al. Evaluation of subjective assessments and objective diagnostic tests for diagnosing tear-film disorders known to cause ocular irritation. Cornea. 1998; 17:38–56.
2. Prabhasawat P, Tseng S C G. Frequent association of delayed tear clearance in ocular irritation. Br. J. Ophthalmology 1998; 82:666–675.
3. Nava A, Barton K, Monroy D C, Pflugfelder S C. The effects of age, gender, and fluid dynamics on the concentration of tear film epidermal growth factor. Cornea 1997; 16:430–438.
4. Jones D T, Monroy D, Pflugfelder S C. A novel method of tear collection: comparison of glass capillary micropipettes win porous polyester rods. Cornea 1997; 16:450–58.
5. Lemp M A. Report of the National Eye Institute/industry workshop on clinical trials in dry eyes. CLAO J 1995;21:222–32.
6. Fleiss J L. Design and Analysis of Clinical Experiments. New York: Wiley, 1986:2–28.
7. McNeil B J, Keeler E, Adelstein J. Primer on certain elements of medical decision making. N Engl J Med 1975; 293: 211–15.
8. Afonso A A, Monroy D, Stern M E, Feuer W J, Tseng S C, Pflugfelder S C. Correlation of tear fluorescein clearance and schirmer test scores with ocular irritation symptoms. *Ophthalmology* 1999;4:803–810.
9. Norn M. Meibomian orifices and Marx's line. Studied by triple vital staining. *Acta Ophthalmol (Copenh)* 1985;63:698–700.
10. Buvat I, De Sousa M C, Di Paola M, et al. Impact of scatter correction in planar scintimammography: a phantom study. *J Nucl Med* 1998;39: 1590–6.

The foregoing detailed description of the preferred embodiments of the invention has been provided for the purposes of illustration and description. The embodiments were chosen and described in order to best explain the principles of the invention and its practical application, modifications and variations of which will be apparent to practitioners skilled in the art. The scope of the invention is intended to be defined by the following claims and their equivalents.

What is claimed is:

1. A process of measuring tear clearance from a mammalian eye, comprising:
   (a) instilling an effective amount of fluorescein dye solution into an inferior conjunctival sac of an eye;
   (b) incubating the fluorescein dye solution in the conjunctival sac for a period of time sufficient to allow dye to mix with tear fluid;
   (c) collecting a sample of the tear fluid from the eye;
   (d) determining the volume of the tear fluid collected; and
   (e) measuring an amount of fluorescence present in the tear fluid by comparison with a color standard.

2. The process according to claim 1, wherein the fluorescein dye solution comprises about 0.5% to about 2% fluorescein in saline.

3. The process according to claim 2, wherein the effective amount of the fluorescein dye solution comprises between about 0.5 microliters and about 5 microliters.

4. The process according to claim 1, wherein tear fluid is collected on a substrate for comparing the amount of fluorescence present in the tear fluid with a color standard.

5. The process according to claim 4, wherein the color standard comprises a color standard plate.

6. The process according to claim 4, wherein the substrate is a member selected from the group consisting of a filter paper strip and a polyester wick.

7. The method of claim 4, wherein measurement of the amount of fluorescence present in the tear fluid is performed by:
   collecting volumes of tear fluid between 0.5 μl and 3 μl on a substrate, and
   comparing the color of the fluorescein-stained substrate to a color standard.

8. The method of claim 7, wherein the color standard comprises a standard visual scale having scores ranging from 0 to 6, wherein a score of 3 corresponds to a fluorometric value of 274 fluorescein units/μl.

9. The process according to claim 1, wherein the amount of fluorescence present in tear fluid is measured directly from an inferior tear meniscus.

10. The process according to claim 9, wherein the amount of fluorescence present in tear fluid is directly measured from the inferior tear meniscus using a color standard viewed simultaneously with the inferior tear meniscus under a biomicroscope.

11. A process of detecting at least one ocular abnormality affecting tear flow, said process comprising:
   (a) instilling an effective amount of fluorescein dye solution into an inferior conjunctival sac of an eye;
   (b) incubating the fluorescein dye solution in the conjunctival sac for a period of time sufficient to allow the dye to mix with tear fluid;
   (c) collecting a sample of tear fluid from the eye;
   (d) determining the volume of tear fluid collected; and
   (e) measuring the amount of fluorescence present in the tear fluid.

12. A process according to claim 11, wherein the ocular abnormality comprises a member selected from the group consisting of meibomian gland disease, conjunctivochalasis, lid laxity, tear outflow obstruction and blink abnormalities.

13. A process according to claim 11, wherein measurement of the amount of fluorescence present in the tear fluid is performed by:
   collecting volumes of tear fluid between 0.5 μl to 3 μl on a substrate, and
   comparing the color of the fluorescein-stained substrate to a color standard.

14. The process according to claim 13, wherein the substrate comprises a member selected from the group consisting of a filter paper strip and a polyester wick.

15. The process according to claim 13, wherein the color standard comprises a standardized visual scale having scores ranging from 0 to 6, wherein a score of 3 corresponds to a fluorophotometric value of 274 fluorescein units/μl.

16. The process according to claim 15, wherein sensitivity of measurements from the standardized visual scale are increased according to correction formula II:

$$\text{SVST (corrected)} = \text{SVST} + \frac{\text{Schirmer score}}{y} \quad \text{II}$$

wherein coefficient y corresponds to an area under a Receiver Operating Characteristic (ROC) curve and the Schirmer score is obtained using Schirmer test strips placed over an eyelid margin.

17. A process of detecting at least one ocular abnormality affecting tear flow, said process comprising:
- (a) instilling an effective amount of fluorescein dye solution into conjunctival sac of an eye;
- (b) incubating the fluorescein dye solution in the conjunctival sac for a period of time sufficient to allow dye to mix with tear fluid;
- (c) examining the eye surface with a biomicroscope to observe corneal fluorescein staining in each of four corneal quadrants;
- (e) measuring fluorescence observed to obtain a corneal fluorescein staining score; and
- (f) correlating the corneal fluorescein staining score with results from a Fluorescein Clearance Test (FCT) corrected according to correction formula I:

$$FCT(\text{corrected}) = FCT + \text{Schirmer score.}(y) \qquad \text{I}$$

wherein coefficient y is calculated from a corresponding area under the Receiver Operating Characteristic (ROC) curve, and the Schirmer score is obtained using Schirmer test strips placed over an eyelid margin.

18. The process according to claim 17, wherein coefficient y is 4.

19. A diagnostic kit for measuring tear clearance comprising:
- (a) an indicator suitable for introduction into an inferior conjunctival sac of an eye, the indicator comprising a member selected from the group consisting of a dye, an enzyme and a chemical; and
- (b) a color standard for measuring indicator present in an inferior meniscus of an eye between about 5 and about 15 minutes after introduction of the indicator to the eye, wherein the color standard comprises a standardized visual scale having scores corresponding to clinically relevant measures of tear clearance.

20. A diagnostic kit for measuring tear clearance comprising:
- (a) a fluorescein dye solution suitable for introduction into an inferior conjunctival sac of an eye;
- (b) a substrate for collecting a sample of tear fluid from the eye; and
- (c) a color standard for measuring the amount of fluorescence preset in the tear fluid,
- wherein the color standard comprises a standardized visual scale having scores corresponding to clinically relevant measures of tear clearance.

21. A diagnostic kit according to claim 20, wherein said fluorescein dye solution is introduced to the eye via a unit-dose dropperette.

22. A diagnostic kit according to claim 21, wherein said unit-dose dropperette administers dosages of about 0.5 microliters to about 5 microliters of fluorescein dye solution.

23. A diagnostic kit according to claim 20, wherein the color standard comprises a color photographic plate, optionally of a size appropriate for placement along a lower eyelid to be viewed under a biomicroscope simultaneously with an inferior tear meniscus.

24. A diagnostic kit according to claim 20, wherein the color standard comprises a standardized visual scale having scores ranging from 0 to 6, wherein a score of 3 corresponds to a fluorophotometric value of 274 fluorescein units/$\mu$l.

25. A diagnostic kit according to claim 24, wherein sensitivity of measurements from the standardized visual scale are improved according to correction formula II:

$$\text{SVST (corrected)} = \text{SVST} + \frac{\text{Schirmer score}}{y} \qquad \text{II}$$

wherein coefficient y corresponds to an area under a Receiver Operating Characteristic (ROC) curve and the Schirmer score is obtained using Schirrner test strips placed over an eyelid margin.

26. A process of measuring tear clearance from a mammalian eye, comprising:
- (a) instilling an effective amount of an indicator solution into an inferior conjunctival sac of an eye, the indicator comprising a member selected from the group consisting of a dye, an enzyme and a chemical;
- (b) incubating the indicator solution in the conjunctival sac for a period of time sufficient to allow indicator to mix with tear fluid; and
- (c) collecting a sample of tear fluid from the eye;
- (d) determining the volume of tear fluid collected; and
- (e) measuring the amount of indicator in the tear fluid by comparison with a color standard, wherein the color standard comprises a standardized visualized scale having scores ranging from 0 to 6, wherein a score of 3 indicates the cut-off value between normality and abnormality.

27. The method of claim 26, wherein said indicator is fluorescein.

28. The method of claim 27, wherein said score of 3 corresponds to a fluorophotometric value of 274 fluorescein units/$\mu$l.

29. A process of measuring tear clearance from a mammalian eye, comprising:
- (a) instilling an effective amount of an indicator solution into an inferior conjunctival sac of an eye, the indicator comprising a member selected from the group consisting of a dye, an enzyme and a chemical;
- (b) incubating the indicator solution in the conjunctival sac for a period of time sufficient to allow indicator to mix with tear fluid; and
- (c) measuring the amount of indicator in the tear fluid by comparison with a color standard, wherein the color standard comprises a standardized visualized scale having scores ranging from 0 to 6, wherein a score of 3 indicates the cut-off value between normality and abnormality.

30. The method of claim 29, wherein said indicator is fluorescein.

31. The method of claim 30, wherein said score of 3 corresponds to a fluorophotometric value of 274 fluorescein units/$\mu$l.

32. The method of claim 30, wherein the indicator is measured between about 5 and 15 minutes after introduction to the eye.

* * * * *